United States Patent
Blackwell et al.

(10) Patent No.: US 9,227,996 B2
(45) Date of Patent: Jan. 5, 2016

(54) **PEPTIDE-BASED QUORUM SENSING INHIBITORS FOR THE ATTENUATION OF VIRULENCE IN *STAPHYLOCOCCUS AUREUS***

(71) Applicant: WISCONSIN ALUMNI RESEARCH FOUNDATION, Madison, WI (US)

(72) Inventors: Helen Blackwell, Middleton, WI (US); Yftah Tal-Gan, Madison, WI (US); Danielle Stacy, San Diego, CA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/109,193

(22) Filed: Dec. 17, 2013

(65) Prior Publication Data
US 2014/0256615 A1 Sep. 11, 2014

Related U.S. Application Data

(63) Continuation of application No. 13/792,977, filed on Mar. 11, 2013, now abandoned.

(51) Int. Cl.
*A61K 38/12* (2006.01)
*C07K 5/12* (2006.01)
*C07K 7/56* (2006.01)
*C07K 7/64* (2006.01)
*A61K 38/00* (2006.01)

(52) U.S. Cl.
CPC . *C07K 5/12* (2013.01); *A61K 38/12* (2013.01); *C07K 7/56* (2013.01); *C07K 7/64* (2013.01); *A61K 38/00* (2013.01)

(58) Field of Classification Search
None
See application file for complete search history.

(56) References Cited

U.S. PATENT DOCUMENTS

| | | |
|---|---|---|
| 6,337,385 B1 | 1/2002 | Muir et al. |
| 6,953,833 B2 | 10/2005 | Muir et al. |
| 7,419,954 B2 | 9/2008 | Muir et al. |
| 8,168,397 B2 | 5/2012 | Charlton et al. |
| 2007/0185016 A1 | 8/2007 | Muir et al. |

FOREIGN PATENT DOCUMENTS

| | | |
|---|---|---|
| WO | WO99/26968 | 6/1999 |
| WO | WO 2009/154988 | 12/2009 |

OTHER PUBLICATIONS

Mar. 4, 2014 memo from Andrew H. Hirshveld providing guidance for 35 USC 101.*
Novick, Richard P. and Geisinger, Edward; "Quorum sensing in staphylococci." Annu. Rev. Genet. (2008) 42 p. 541-64.*
Fowler, Sarah A. et al; "Design and synthesis of macrocyclic peptomers as mimics of a quorum sensing signal from *Staphylococcus aureus*." Org. Lett. (2008) 10(12) p. 2329-2332.*
Aurelio, Luigi et al, "Synthetic preparation of n-methyl alpha amino acids." Chem. Rev. (2004) 104 p. 5823-5846.*
Amara et al. (published online Nov. 18, 2010) "Macromolecular Inhibition of Quorum Sensing: Enzymes, Antibodies, and Beyond," *Chem. Rev.* 111(1):195-208.
Broderick et al. (Jun. 2013) "Surface Coatings that Promote Rapid Release of Peptide-Based AgrC Inhibitors for Attenuation of Quorum Sensing in *Staphylococcus aureus*." *Adv. Healthcare Mater.* 3:97-105.
Chan et al. (Sep. 2004) "Virulence Regulation and Quorum Sensing in Staphylococcal Infections: Competitive AgrC Antagonists as Quorum Sensing Inhibitors," *J. Med. Chem.* 47(19):4633-4641.
Fowler et al. (May 2008) "Design and Synthesis of Macrocyclic Peptomers as Mimics of a Quorum Sensing Signal from *Staphylococcus aureus*," *Org. Lett.* 10(12):2329-2332.
George et al. (Mar. 2008) "Cyclic Peptide Inhibitors of Staphylococcal Virulence Prepared by Fmoc-Based Thiolactone Peptide Synthesis," *J. Am. Chem. Soc.* 130(14):4914-4924.
George et al. (May 2007) "Molecular Mechanisms of agr Quorum Sensing in Virulent Staphylococci," *ChemBioChem.* 2007, 8, 847-855.
Chose et al. (1999) "A Knowledge-Based Approach in Designing Combinatorial or Medicinal Chemistry Libraries for Drug Discovery", J. Combin. Chem., 1(1):55-68.
Gorske et al. (Mar. 2006) "Interception of Quorum Sensing in *Staphylococcus aureus*: A New Niche for Peptidomimetics," *Org. Biomol. Chem.* 4:1441-1445.
Jarraud et al. (Nov. 2000) "Exfoliatin-Producing Strains Define a Fourth agr Specificity Group in *Staphylococcus aureus*," *J. Bacteriol.* 182(22):6517-6522.
Ji et al. (Jun. 1997) "Bacterial Interference Caused by Autoinducing Peptide Variants," *Science.* 276(5321):2027-2030.
Kaufmann et al. (Jun. 2008) "Bacterial Quorum Sensing: A New Target for Anti-Infective Immunotherapy," *Exp. Opin. Biol. Ther.* 8(6)719-724.
Kirchdoerfer et al. (Mar. 2011) "Structural Basis for Ligand Recognition and Discrimination of a Quorum-Quenching Antibody," *J. Biol. Chem.* 286(19):17351-17358.
Li et al. (Feb. 2011) "Lactobacillus *reuteri*-Produced Cyclic Dipeptides Quench agr-Mediated Expression of Toxic Shock Syndrome Toxin-1 in Staphylococci," *Proc. Natl. Acad. Sci. U. S. A.* 2011, 108, 3360-3365.
Lyon et al. (Aug. 6, 2002) "Key Determinants of Receptor Activation in the agr Autoinducing Peptides of *Staphylococcus aureus*," *Biochemistry.* 41(31):10095-10104.

(Continued)

*Primary Examiner* — Maury Audet
*Assistant Examiner* — Fred Reynolds
(74) *Attorney, Agent, or Firm* — Lathrop & Gage LLP

(57) ABSTRACT

Compounds that affect quorum sensing (QS) in *Staphylococcus aureus* and related *Staphylococcus* species (e.g., *S. epidermidis*). Compounds which modulate one or more of the four AgrC receptors of *Staphylococcus* species, particularly of *Staphylococcus aureus*. Modulation includes inhibition or activation of one or more of these four AgrC receptors. These compounds are useful for bacterial interference and are useful for treating bacterial infections, particularly staphylococcal infection. Treatment can include combination of one or more of the compounds of the invention in combination with one or more antibiotics.

26 Claims, 6 Drawing Sheets

(56) References Cited

OTHER PUBLICATIONS

Lyon et al. (Nov. 2000) "Rational Design of a Global Inhibitor of the Virulence Response in *Staphylococcus aureus*, Based in Part on the Localization of the Site of Inhibition to the Receptor-Histidine Kinase, AgrC," *Proc. Natl. Acad. Sci. U. S. A.* 2000, 97, 13330-13335.

Lyon et al. (Sep. 2004) "Peptide Signaling in *Staphylococcus aureus* and Other Gram-positive Bacteria," *Peptides*. 25(9):1389-1403.

Malone et al. (Aug. 2007) "Biosynthesis of *Staphylococcus aureus* Autoinducing Peptides by Using the Synechocystis DnaB Mini-intein," *Appl. Environ. Microbiol.* 73:6036-6044.

Mayville et al. (Feb. 1999) "Structure-Activity Analysis of Synthetic Autoinducing Thiolactone Peptides from *Staphylococcus aureus* Responsible for Virulence," *Proc. Natl. Acad. Sci. U. S. A.* 1999, 96, 1218-1223.

McDowell et al. (Jul. 2001) "Structure, Activity and Evolution of the Group I Thiolactone Peptide Quorum-Sensing System of *Staphylococcus aureus*," *Mol. Microbiol.* 41(2):503-512.

Rasko et al. (Jan. 2010) "Anti-virulence strategies to combat bacteria-mediated disease," *Nat. Rev. Drug Disc.* 9(2):117-128.

Sintim et al. (Jun. 2010) "Paradigm Shift in Discovering Next-Generation Anti-Infective Agents: Targeting Quorum Sensing, c-di-GMP Signaling and Biofilm in Bacteria with Small Molecules," *Future Med. Chem.* 2010, 2,1005-1035.

Stacy (Apr. 6, 2012) "Attenuation of Quorum Sensing and Virulence in the Pathogen *Staphylococcus aureus* Using Synthetic Autoinducer Mimics," In; The Lincoln Seminar Series. The University of Wisconsin—Madison. Madison, Wisconsin.

Stacy et al. (Apr. 13, 2012) "Attenuation of Quorum Sensing and Virulence in the Pathogen *Staphylococcus aureus* Using Synthetic Autoinducer Mimics," In; Perlman Symposium on Antibiotic Discovery and Development. Madison, Wisconsin.

Stevens et al. (Dec. 2010) "Mechanisms and synthetic modulators of AHL-dependent gene regulation," *Chem. Rev.* 111(1):4-27.

Tal-Gan et al. (Aug. 7-8, 2008) "The Application of Peptidomimetics to Study Quorum Sensing in *Staphylococcus aureus*," In; The 6$^{th}$ Peptoid Summit. Berkeley, California.

Tal-Gan et al. (May 2013) "Highly Potent Inhibitors of Quorum Sensing in *Staphylococcus aureus* Revealed Through a Systematic Synthetic Study of the Group-III Autoinducing Peptide," *J. Amer. Chem. Soc.* 135(21):7869-7882.

Tal-Gan et al. (Nov. 2013) "Structural Characterization of Native Autoinducing Peptides and Abiotic Analogues Reveals Key Features Essential for Activation and Inhibition of an AgrC Quorum Sensing Receptor in *Staphylococcus aureus*" *J. Am. Chem. Soc.* 135(49):18436-18444.

Tal-Gan et al. (Jan. 2014) "N-Methyl and peptoid scans of an autoinducing peptide reveal new structural features required for inhibition and activation of AgrC quorum sensing receptors in *Staphylococcus aureus*" *Chem. Comm.* 50:3000-3003.

Tal-Gan et al. (Feb. 18-19, 2012) "Development of Peptide-Based Tools to Study Quorum Sensing in *Staphylococcus aureus*," In; Gordon Research Conference: Peptides, Chemistry and Biology of (GRS). Ventura, California.

Thoendel et al. (Dec. 2010) "Peptide Signaling in the Staphylococci," *Chem. Rev.* 111(1):117-151.

Wright et al. (Nov. 2004) "Hydrophobic Interactions Drive Ligand-Receptor Recognition for Activation and Inhibition of Staphylococcal Quorum Sensing," *Proc. Natl. Acad. Sci. U. S. A.* 101(46):16169-16173.

\* cited by examiner

H—Ile—Asn—Cys—Asp—Phe—Leu—Leu
AIP-III

H-N-Ile-Asn—Cys—Asp—Phe—Leu—Leu
AIP-III nI1

Ile-N-Asn—Cys—Asp—Phe—Leu—Leu
AIP-III nN2 DKP

H—Ile—Asn—Cys-N-Asp-Phe—Leu—Leu
AIP-III nD4

H—Ile—Asn—Cys—Asp-N-Phe-Leu—Leu
AIP-III nF5

H—Ile—Asn—Cys—Asp—Phe-N-Leu-Leu
AIP-III nL6

H—Ile—Asn—Cys—Asp—Phe—Leu-N-Leu
AIP-III nL7

H-NMe-Ile-Asn—Cys—Asp—Phe—Leu—Leu
AIP-III N-Me-I1

H-Ile-NMe-Asn-Cys—Asp—Phe—Leu—Leu
AIP-III N-Me-N2

H—Ile—Asn—NMe-Cys-Asp-Phe-Leu-Leu
AIP-III N-Me-C3

H—Ile—Asn—Cys-NMe-Asp-Phe-Leu-Leu
AIP-III N-Me-D4

H—Ile—Asn—Cys-Asp-NMe-Phe-Leu-Leu
AIP-III N-Me-F5

H—Ile—Asn—Cys-Asp-Phe-NMe-Leu-Leu
AIP-III N-Me-L6

H—Ile—Asn—Cys-Asp-Phe-Leu-NMe-Leu
AIP-III N-Me-L7

FIG. 4

PEPTIDE-BASED QUORUM SENSING INHIBITORS FOR THE ATTENUATION OF VIRULENCE IN *STAPHYLOCOCCUS AUREUS*

STATEMENT REGARDING GOVERNMENT SUPPORT

This invention was made with government support under N00014-07-1-0255 awarded by the NAVY/ONR. The government has certain rights in the invention.

CROSS-REFERENCE TO RELATED APPLICATIONS

This application is a continuation of and claims the benefit of copending U.S. application Ser. No. 13/792,977, filed Mar. 11, 2013, which is hereby incorporated by reference in its entirety to the extent not inconsistent with the disclosure herewith.

BACKGROUND OF THE INVENTION

Many bacteria utilize small molecule or peptidic signals to assess their local population densities in a process termed quorum sensing (QS). [1-3] This chemical signaling process effectively allows bacteria to "count" themselves and behave as a group at high cell number. While the specifics may vary between species, QS circuits share general organizing principles: bacteria produce, secrete, and detect signal molecules referred to as autoinducers. At high population densities in a given environment, the autoinducers will reach a sufficiently high concentration to bind and activate their cognate (intracellular or extracellular) receptors. Signal:receptor binding then alters the expression of genes involved in bacterial group behaviors, such as swarming, sporulation, bioluminescence, conjugation, biofilm formation, and virulence factor production. [4-6] These phenotypes can have widespread and sometimes devastating effects on human health, agriculture, and the environment.[7, 8] For example, pathogenic bacteria utilize QS to launch synchronized attacks on their hosts only after they have achieved a high cell density, thereby overwhelming the defense mechanisms of the host.[9-11] As several prevalent human pathogens (e.g., *Staphylococcus aureus*) use QS to control virulence, QS has received considerable recent attention as a new anti-infective target.[12] There has been significant interest in the development of non-native ligands (e.g., small molecule and peptides) capable of blocking QS pathways. In contrast to antibiotics, which target bacterial pathways that are essential for survival, QS antagonists provide an alternative anti-infective therapy that does not place selective pressure on the bacterial population to develop resistance.[13, 14] This is especially important in the case of *S. aureus*, which rapidly develops resistance to antibiotics, including resistance to the once last-resort antibiotic vancomycin.[15]

*S. aureus* is a Gram-positive bacterium that uses QS to establish both acute and chronic infections.[16, 17] This pathogen produces an impressive arsenal of virulence factors, including tissue-degrading enzymes, immune evasion factors, and pore-forming toxins (hemolysins), all of which are regulated by the accessory gene regulator (agr) QS system. [18-20] The agr system has four components, termed AgrA-D, as illustrated in FIG. 1A, and is centered on the autoinducing peptide (AIP) QS signal. AgrB is an integral membrane endopeptidase that converts the precursor of the AIP signal, AgrD, to the mature AIP. This conversion involves cyclization of AgrD via a cysteine sulfhydryl group and its C-terminus to form the AIP as a 16-atom thiolactone macrocycle with an N-terminal exocyclic tail (shown in FIG. 1B). AgrB is also involved in the secretion of AIP across the cell membrane. Once a threshold concentration of AIP is reached in a given environment, the AIP ligand binds to its target receptor AgrC, a transmembrane histidine kinase. The AIP:AgrC complex acts to phosphorylate the response regulator, AgrA. Phosphorylated AgrA then binds to the P2 and P3 promoters to autoinduce the agr system and upregulate RNAIII transcription. [21] RNAIII thus represents the main effector of the agr system and regulates the expression of many virulence factors and surface proteins associated with biofilm production.[22]

There is a hypervariable region within the *S. aureus* agr operon that has led to the classification of four agr specificity groups of *S. aureus* (I-IV) with distinct AIP and AgrC sequences.[23-25] The structures of the four AIP signals (I-IV) are shown in FIG. 1B. The four AIP signals have a conserved 16-atom thiolactone macrocycle, and AIPs I and IV share a nearly identical primary sequence, while AIP-II and AIP-III have more dissimilar primary sequences.

The four different agr groups have been correlated with specific disease types: group-I and -II are associated with the majority of invasive infections,[26-28] while group-IV is considered rare and limited to exfoliative toxin-related syndromes8 26] Group-III *S. aureus* has recently been reported to be the most abundant group in nasal carriage cases and to be predominately responsible for toxic shock syndrome (TSS) in humans.[26, 27] Toxic shock syndrome toxin-1 (TSST-1) is the causative agent all cases of menstrual TSS and most cases of nonmenstrual TSS.[26, 29] Notably, TSST-1 production is directly regulated by the agr-III QS system (FIG. 1A).[18, 29, 30] Methods to inhibit the agr-III system in *S. aureus* could provide new insights into and therapeutic strategies for this deadly disease.

QS is dependent on autoinducer:receptor binding, and the development of chemical agents capable of blocking this binding event have been a focus of considerable research.[31-33] Both small molecules and macromolecules have been utilized to block native autoinducer binding, largely in Gramnegative bacteria.[34, 35] Such abiotic agents can be useful in anti-infective treatments.[36-38] The development of small molecules that affect AgrC signaling in *S. aureus* has proceeded more slowly.

Janda et al. [35, 44] have recently reported a complimentary strategy based on antibodies that sequester the AIP ligand away from AgrC and effectively "quench" QS in group-IV *S. aureus*. McCormick and co-workers have reported that naturally occurring cyclic dipeptides produced by *Lactobacillus reuteri* can modulate the agr system in *S. aureus*.[29]

Early studies of the AgrC systems reported that each of the native AIPs were capable of cross-inhibiting the other three, non-cognate receptors.[23, 45-47] This activity was suggested to provide each group some competitive advantage when establishing an infection, and to explain in part the predominance of a single *S. aureus* group in many infection types.[23, 48] Given the prevalence of group-I and -II systems in clinically relevant infections, AIP-I and AIP-II have so far received the most scrutiny for the design of AgrC modulators. [24, 45, 46, 49-52]

Studies by Muir, Novick, Williams, and co-workers examined the structure activity relationship (SAR) of AIP-I and AIP-II, [53-55] and reported certain non-native mimetics of these peptides that were capable of inhibiting both their cognate and non-cognate AgrC receptors in *S. aureus*. There are two components to AIP:AgrC interactions: initial recognition and induction of an allosteric response that drives activation. The core AIP-II macrocycle was reported to be important for recognition because linear native peptides and mimetics of AIP-II were completely inactive.[45] In addition, these studies reported that the two structural elements of AIPs, the macrocycle and the exocyclic tail, are responsible for AgrC: AIP recognition and AgrC activation, respectively. [55] Interactions of AIPs with non-cognate AgrC receptors were reported to be inhibitory, namely through AIP:AgrC recognition, alterations to the exocyclic tails did not significantly affect cross-inhibition. The AIP macrocycle alone is reported sufficient for cross-group inhibitory activity. Within the AIP-I and AIP-II macrocycles, the hydrophobic residues at the C-termini were reported to be essential for cognate and non-cognate AgrC recognition.[24, 45, 49] Consistent with these observations, Muir et al. reported several potent and global inhibitors of all four AgrC receptors.[49] The most active inhibitor was reported to be a truncated version of AIP-I that lacked an exocyclic tail and had an aspartic acid to alanine mutation in the macrocyclic core (tAIP-I D2A):

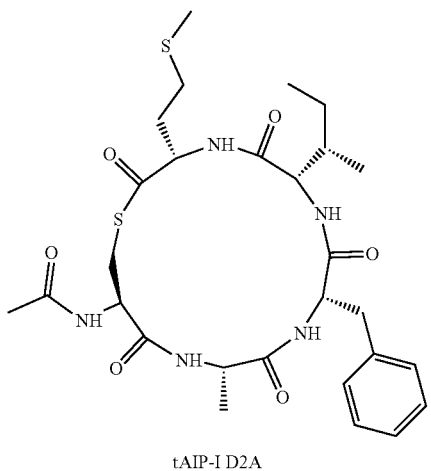 [SMILES: CC[C@H](C)[C@@H]1NC(=O)[C@H](Cc2ccccc2)NC(=O)[C@H](C)NC(=O)[C@@H](NC(C)=O)CSC(=O)[C@H](CCSC)NC1=O]

tAIP-I D2A

Peptidomimetics are a powerful tool for studying and understanding SARs of peptides and proteins. [67] Modifications can be introduced to gather information regarding the importance of specific amide and hydrogen bonds within a peptide backbone and to identify conformational restrictions and structural elements important to overall activity while simultaneously enhancing pharmacological properties. [68-73] Peptidomimetics, with enhanced metabolic stability and permeability, can be useful as drug leads. [67, 74] For instance, N-methyl amino acids and N-substituted glycine derivatives (peptoids) can be inserted into or formed into peptides generating fully or partially N-methylated peptides, peptoids or peptide-peptoid (peptomer) hybrids which can be used to provide valuable SAR insights.

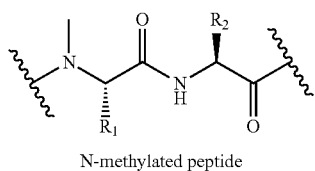

N-methylated peptide

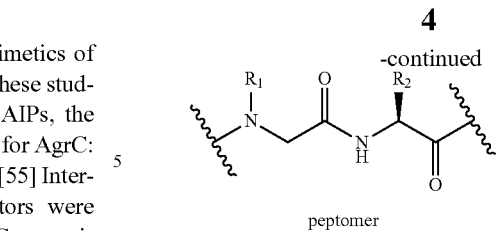

peptomer

For example, Muir and co-workers [51] performed a N-methyl scan of the truncated version of AIP-II pointing to the utility of such studies for AIP SAR.

The SARs that dictate the activity of AIP-III remain largely unknown, and mimetics thereof are yet to be reported.

AIP-III

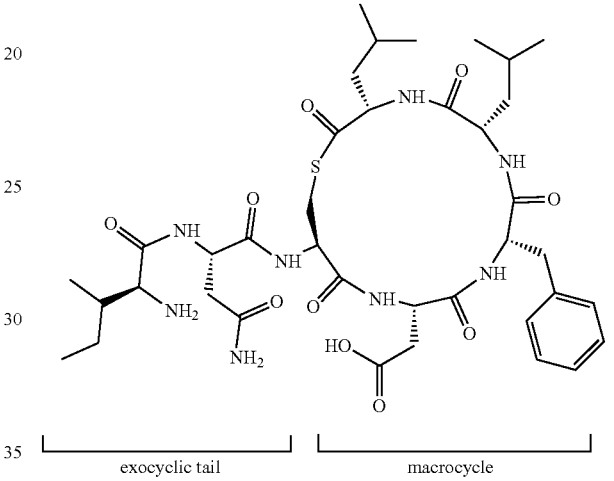

Molecules which affect QS in group-III *S. aureus* are of particular interest because of the prevalence of infections of these group-III species in human TSS.

SUMMARY OF THE INVENTION

This invention provides compounds that are useful for bacterial interference. The invention provides compounds that are useful in the treatment of bacterial infection and related conditions. More specifically the invention provides compounds that are useful in the treatment of "staph" infections (infections caused by *Staphylococcus* bacteria) and particularly infections of *Staphylococcus aureus*.

The invention provides compounds that affect quorum sensing (QS) in *Staphylococcus aureus* and related *Staphylococcus* species (e.g., *S. epidermidis*). More specifically the invention provides compounds which modulate one or more of the four AgrC receptors of *Staphylococcus* species, particularly of *Staphylococcus aureus*. Modulation includes inhibition or activation of one or more of these four AgrC receptors.

The invention provides compounds which inhibit one or more of the four AgrC receptors of *Staphylococcus* species, particularly of *Staphylococcus aureus*. In specific embodiments, compounds which inhibit three or four of the AgrC receptors are provided. In additional embodiments, compounds which inhibit all four of the AgrC receptors are provided. In yet additional embodiments, compounds which inhibit all four of the AgrC receptors with picomolar $IC_{50}$ values are provided.

The invention provides compounds which activate one or more of the four AgrC receptors of *Staphylococcus* species, particularly of *Staphylococcus aureus*. In specific embodiments, the invention provides compounds which activate AgrC-III.

Certain compounds of the invention block hemolysis by wild-type *Staphylococcus aureus*, which is a virulence phenotype under the control of QS. Certain compounds of the invention block hemolysis by wild-type *Staphylococcus aureus* at picomolar levels. Certain compounds of the invention reduce TSST-1 production levels in a wild-type *Staphylococcus aureus* group-III strain. Certain compounds of the invention reduce TSST-1 production levels in a wild-type *Staphylococcus aureus* group-III strain by over 80%.

In specific embodiments, compounds of the invention are useful for the treatment of infections involving *Staphylococcus aureus* group-III strains and particularly for the treatment of Toxic shock syndrome.

In specific embodiments, compounds of the invention modulate biofilm formation by *Staphylococcus* species, particularly *Staphylococcus aureus* and more particularly *Staphylococcus aureus* group-III strains.

The invention provides compounds of formula I:

and salts thereof where:

L is a divalent linker moiety 3 to 10 atoms in length;

Z is a divalent linker moiety 3 to 14 atoms in length;

$R_1$ and $R_2$ are independently selected from hydrogen, an optionally substituted alkyl group having 1-6 carbon atoms, an optionally substituted aryl group or an optionally substituted heteroaryl group;

$R_6$ and $R_7$ are independently selected from hydrogen, an optionally substituted alkyl group having 1-8 carbon atoms, an optionally substituted aryl group or an optionally substituted heteroaryl group; where, when $R_1$ is a group other than hydrogen or a methyl group, $R_6$ is a hydrogen or a methyl group and when $R_2$ is a group other than hydrogen or a methyl group, $R_7$ is a hydrogen or a methyl group;

$R_{10}$ is hydrogen or a methyl group;

$R_5$ is an optionally substituted alkyl group having 1-8 carbon atoms, an optionally substituted aryl group, an optionally substituted heteroaryl group, an optionally substituted heterocyclic or $R_5$ is:

$H_2N—CHR_{12}—$, $H_2N—CHR_{12}—CO—NR_{14}—$, $H_2N—CHR_{12}—CO—NR_{14}—CHR_{12}—$, $R_{15}—CO—NR_{14}—$, or $R_{15}—CO—NR_{14}—CHR_{12}$, where each $R_{12}$ is hydrogen, an optionally substituted alkyl group having 1-6 carbon atoms, an optionally substituted aryl group or an optionally substituted heteroaryl group; $R_{14}$ is hydrogen, an optionally substituted alkyl group having 1-8 carbon atoms, an optionally substituted aryl group or an optionally substituted heteroaryl group; and $R_{15}$ is an optionally substituted alkyl group having 1-8 carbon atoms, an optionally substituted aryl group or an optionally substituted heteroaryl group where, when $R_5$ is $H_2N—CHR_{12}—CO—NR_{14}—$ and $R_{12}$ is a group other than hydrogen or a methyl, $R_{14}$ is hydrogen or a methyl group.

The term "atoms in length" refers to the shortest number of atoms directly bonded between the points of attachment of L and Z in the formulas herein. If there are two or more possible ways to calculate the number of atoms bonded between the attachment points, the shortest number of atoms is that which is intended to be limited by the recited range.

Substitution when present includes substitution with one or more non-hydrogen groups selected an from halogen, hydroxyl, alkyl having 1-3 carbon atoms, amino-substituted alkyl having 1-4 carbon atoms, alkoxy having 1-3 carbon atoms, amino, alkylamino having 1-3 carbon atoms, dialkyl amino where the alkyl group has 1-3 carbon atoms, aryl, haloalkyl having 1-3 carbon atoms, phenyl, benzyl, phenoxy, benzyloxy, oxo (═O), sulfhydryl, alkylthio having 1-3 carbon atoms, $—CO_2R$ where R is hydrogen or an alkyl having 1-3 carbon atoms, —COR, where R is H or an alkyl having 1-3 carbon atoms, $—CO—NR_2$, where each R is independently hydrogen or alkyl having 1-3 carbon atoms, azido ($N_3—$), nitro, cyano, isocyano, thiocyano, or isothiocyano. Substitution of aryl or heteroaryl groups include substitution in which substituents on two ring atoms together with the ring atom or atoms to which they are attached form a 5-8 member ring which can contain 0 (carbocyclic) or 1-3 heteroatoms (particularly N, O or S).

Substitution of alkyl groups includes substitution with one or more optionally substituted aryl groups, heteroaryl groups, carbocyclic groups or heterocyclic groups, where substitution if present includes substitution with one or more halogens, hydroxyls, alkyl groups, amino, alkylamino or dialkyl amino groups.

In specific embodiments, L is a divalent moiety $—(CH_2)_l$, where l is 3-8 and one, two or three of the $—CH_2—$ moieties therein are optionally replaced with O, S, CO, or —NH—, and/or a $—CH_2—CH_2—$ therein is optionally replaced with a double bond, a phenylene moiety or a cyclohexylene moiety.

In specific embodiments, L is $—(CH_2)_{1-4}—S—CO—$, $—(CH_2)_{1-4}—O—CO—$, $—(CH_2)_{1-4}—NH—CO—$, $—(CH_2)_{1-2}—O—(CH_2)_{1-2}—CO—$, $—(CH_2)_{2-5}—CO—$, $—CO—(CH_2)_{1-4}—CO—$, or $—CH_2—NHCONH—CH_2—$.

In more specific embodiments, L is $—CH_2—X—CO—$, where X is, S, O or NH.

In more specific embodiments, L is $—CH_2—S—CO—$, or $—CH_2—CH_2—S—CO—$.

In specific embodiments, Z is selected from:

(i) a $—NR_9—(CH_2)_n—CO—$ linker, where n is 1 to 9;

(ii) a $—NR_9—(CH_2)_n—CO—NR_8—CH(R_3)—CO—$ linker; or (ii) a $—NR_9—CH(R_4)—CO—NR_8—CH(R_3)—CO—$ linker, wherein $R_3$ is hydrogen, an optionally substituted alkyl group having 1-6 carbon atoms, an optionally substituted aryl group, an optionally substituted heteroaryl group or an optionally substituted heterocyclic group;

$R_4$ is hydrogen, or an optionally substituted alkyl group having 1-3 carbon atoms;

$R_9$ and $R_8$ are independently selected from hydrogen, an optionally substituted alkyl group having 1-8 carbon atoms, an optionally substituted aryl group, an optionally substituted heteroaryl group, or an optionally substituted heterocyclic group; wherein when $R_3$ is a group other than hydrogen or a methyl group, $R_8$ is a hydrogen or a methyl group and when $R_4$ is a group other than hydrogen or a methyl group, $R_9$ is a hydrogen or a methyl group. In specific embodiments, n is 1-7 or n is 2-6, n is 5-8, n is 5-7 or n is 3.

In specific embodiments $R_3$ is an aryl-substituted alkyl group. In specific embodiments $R_3$ is an aryl-substituted methyl group. In specific embodiments $R_3$ is an optionally substituted benzyl group. In specific embodiments $R_3$ is a 4-OH-substituted benzyl group. In specific embodiments, $R_3$ is a heteroaryl-substituted alkyl group. In specific embodiments, $R_3$ is an indoyl-substituted alkyl group. In specific embodiments $R_8$ is an aryl-substituted alkyl group. In specific embodiments $R_8$ is an aryl-substituted methyl group. In specific embodiments $R_8$ is an optionally substituted benzyl group. In specific embodiments $R_8$ is a 4-OH-substituted benzyl group. In specific embodiments, $R_8$ is a heteroaryl-substituted alkyl group. In specific embodiments, $R_8$ is an indoyl-substituted alkyl group.

In specific embodiments, Z is —NH—$(CH_2)_n$—CO—, where n is 1-7, n is 1-5, n is 1 or n is 2. In specific embodiments, Z is —$NR_9$—$CH(R_4)$—CO—$NR_8$—$CH(R_3)$—CO—. In specific embodiments, $R_3$ is a hydrogen and $R_8$ is a group other than a hydrogen. In specific embodiments, $R_4$ is a hydrogen and $R_9$ is a group other than a hydrogen. In specific embodiments, $R_8$ is a hydrogen or a methyl group and $R_3$ is an optionally substituted aryl group or an optionally substituted heteroaryl group. In specific embodiments, $R_9$ is a hydrogen or a methyl group and $R_4$ is an optionally substituted alkyl group having 1-3 carbon atoms.

In specific embodiments, Z is:

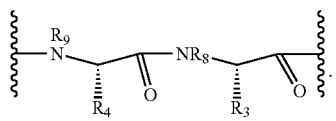

In specific embodiments, $R_3$ is hydrogen and $R_8$ is independently selected from an optionally substituted alkyl group having 1-8 carbon atoms, an optionally substituted aryl group or an optionally substituted heteroaryl group. More specifically $R_8$ is an optionally substituted aryl group. More specifically $R_8$ is an optionally substituted phenyl group. More specifically $R_8$ is an aryl or heteroaryl-substituted alkyl group. More specifically $R_8$ is an aryl or heteroaryl-substituted methyl group. More specifically, $R_8$ is an unsubstituted alkyl having 1-6 carbon atoms, a benzyl, a 4-OH benzyl, a (1H-indo-3-yl)methyl, or a (5-OH-1H-indo-3-yl)methyl. In specific embodiments, $R_8$ or $R_9$ can be a substituted phenyl ring or benzyl ring in which two ring substituents together form a 5- or 6-member saturated or unsaturated ring having 1 or 2 nitrogens, oxygens or both. In specific embodiments, $R_8$ or $R_9$ can independently be piperonyl groups.

In specific embodiments, $R_4$ is hydrogen, or an optionally substituted alkyl group having 1-3 carbon atoms; and $R_9$ is an optionally substituted alkyl group having 1-8 carbon atoms, an optionally substituted aryl group or an optionally substituted heteroaryl group. In an embodiment, $R_8$ and $R_9$ are both hydrogens. In an embodiment, $R_9$ is hydrogen or methyl and $R_4$ is hydrogen, methyl, or —$CH_2$—COOH. In an embodiment, $R_9$ is hydrogen, methyl or —$CH_2$—COOH and $R_4$ is hydrogen or methyl. In an embodiment, $R_1$ and $R_2$ are independently alkyl groups having 2-6 carbon atoms and $R_6$ and $R_7$ are hydrogens.

The invention provides a method for regulating virulence in *Staphylococcus* which comprises the step of contacting the bacterium or a biofilm of said bacterium with one or more compounds of formulas I, IA or II. In specific embodiments, virulence is attenuated.

In a specific embodiment, the invention provides a method of inhibiting biofilm formation or for dispersing an already formed biofilm by contacting the bacterium or biofilm with a compound of formula I. In a specific embodiment, the invention provides a method of inhibiting biofilm formation or for dispersing an already formed biofilm by contacting the bacterium or biofilm with a compound of formula III.

In another aspect, the invention provides an improved solid-phase synthesis protocol for the synthesis of certain cyclic peptides that involves a chemoselective thiol-thioester exchange in the macrocyclization step. This method is illustrated in examples herein and is useful for the synthesis of compounds of this invention.

The invention provides pharmaceutical compositions comprising a pharmaceutically effective amount of one or more of the compounds of formulas herein and a pharmaceutically acceptable carrier. In specific embodiments, the one or more compounds exhibit activation of an AgrC receptor. In specific embodiments, the one or more compounds exhibit activation of the AgrC receptor. In specific embodiments, the one or more compounds exhibit inhibition of an AgrC receptor. In specific embodiments, the invention provides pharmaceutical compositions comprising a pharmaceutically effective amount of two or more of the compounds of formulas herein and a pharmaceutically acceptable carrier. In a specific embodiment, the invention provides pharmaceutical compositions comprising a pharmaceutically effective amount of two or more of the compounds of formulas herein and a pharmaceutically acceptable carrier wherein the two or more compounds exhibit differences in inhibition or activation of the AgrC receptors. More specifically, in such compositions the two or more compounds exhibit group-selective inhibition for one or more of the AgrC receptors.

Other embodiments and aspects of the invention will become apparent on review of the following detailed description, drawings and examples.

BRIEF DESCRIPTION OF THE FIGURES

(FIG. 1A) (a) The precursor peptide AgrD is processed by AgrB. (b) The mature AIP signal is secreted across the cell membrane. (c) AIP binds the extracellular domain of AgrC. (d) The histidine kinase domain of AgrC phosphorylates AgrA. (e) AgrA binds the P2 and P3 promoters to autoactivate the agr system and upregulate RNAIII transcription. (f) In selected *S. aureus* strains, RNAIII promotes the production of toxic shock syndrome toxin-1 (TSST-1). FIG. 1B provides the structures and sequences of the four AIP signals (I-IV) corresponding to the four *S. aureus* groups.

FIG. 4 illustrates exemplary peptidomimetics of this invention.

DETAILED DESCRIPTION OF THE INVENTION

Figure 1:
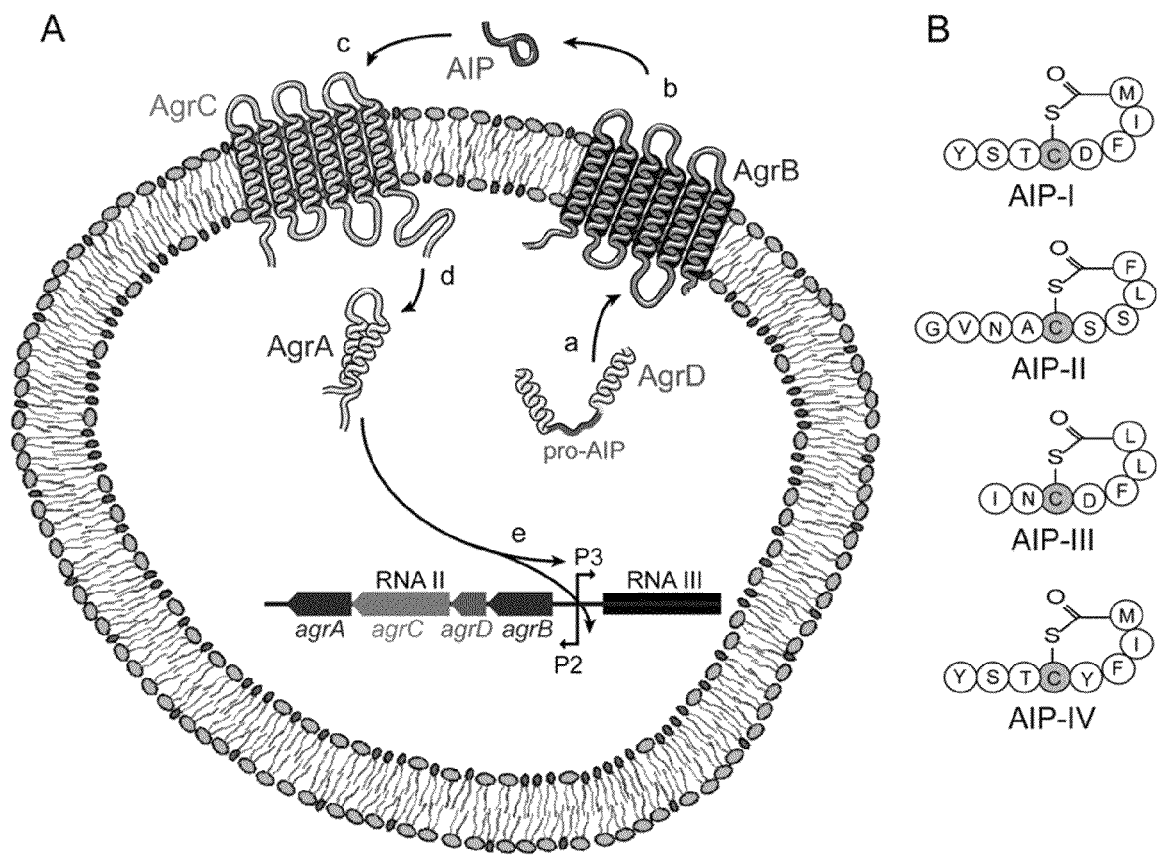
FIGS. 1A-B provides a schematic illustration of the agr quorum sensing circuit in *S. aureus*.
Figure 2A:
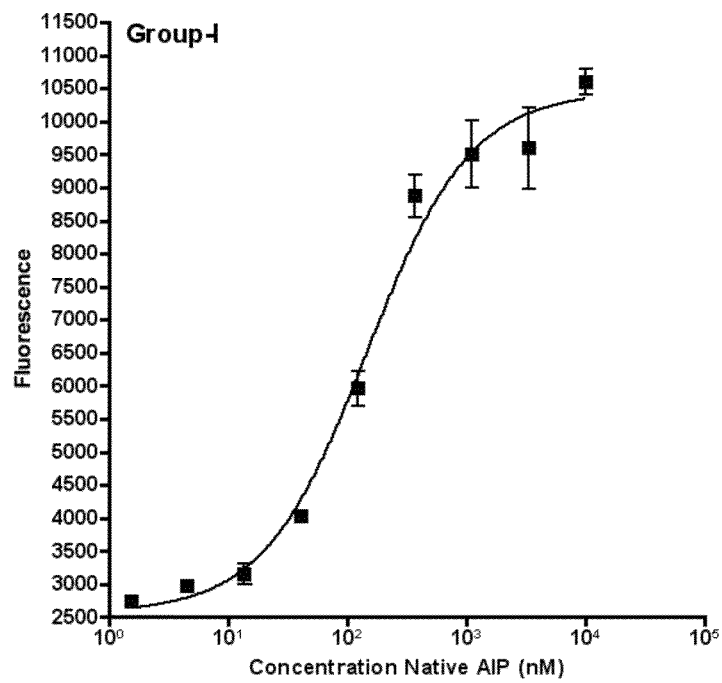
FIGS. 2A-2D provides a set of four competition dose response agonism curves (A-D) for the native AIPs (I-IV) in the presence of AIP-III D4A at 2 nM (group-I (2A) and group-II (2B)) or 0.3 nM (group-III (2C) and group-IV (2D)) in the group-I-IV fluorescence reporter strains. Error bars indicate standard error of the mean of triplicate values.
Figure 2B:
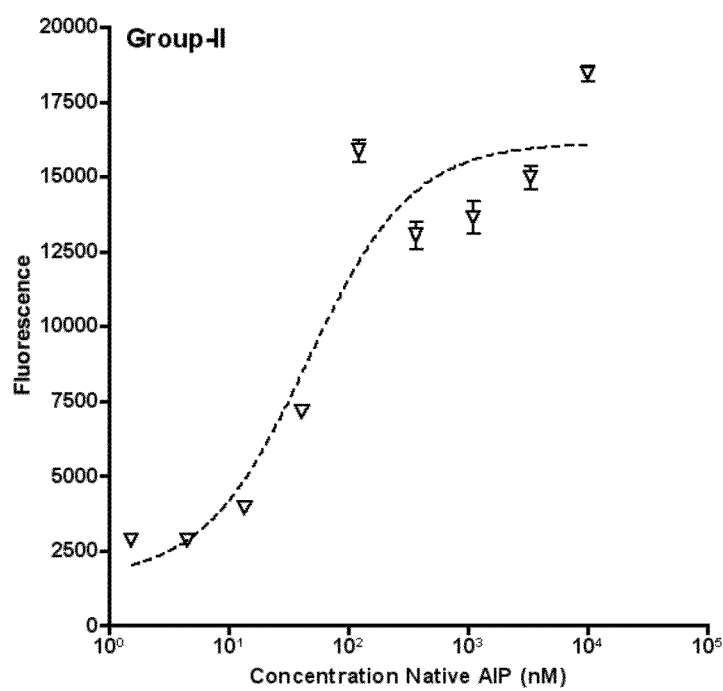
Figure 2C:
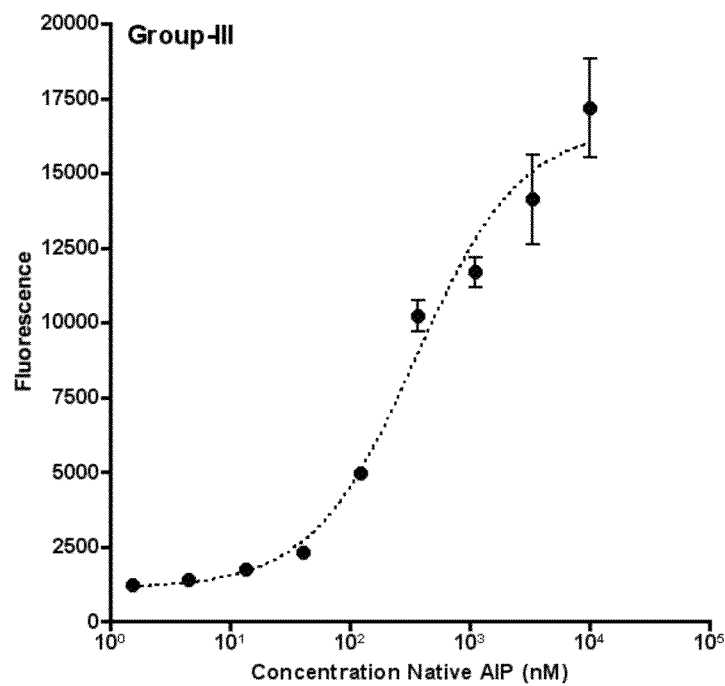
Figure 2D:
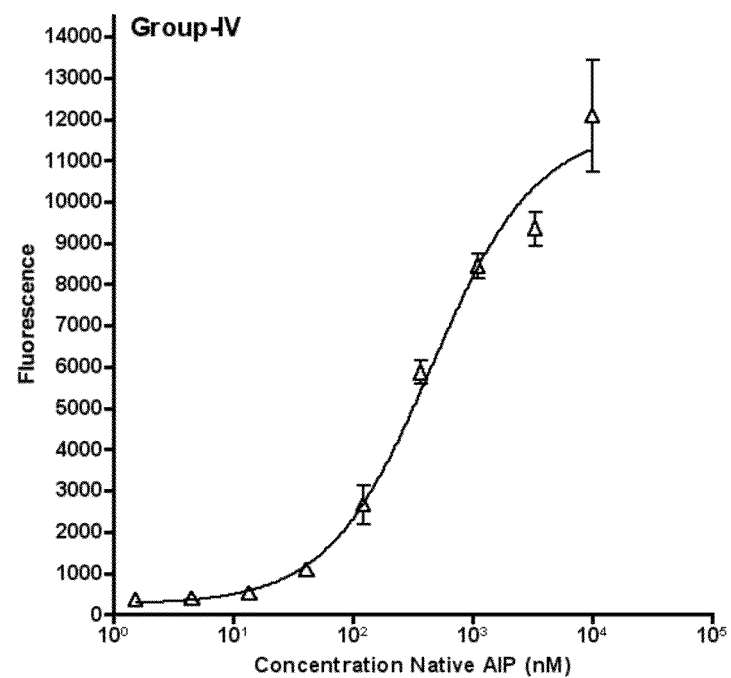

This invention is based at least in part on the synthesis of structural variants of the AIP-III cyclic peptide and assessment of the activity of API-III structural variants for modulation of one or more of the four AgrC receptors of *Staphylococcus aureus*. Structural variants include those generated by alanine, D-amino acid, N-methylated amino acid and peptoid scans of AIP-III. Additional structural variants examined include double- and triple mutated variants, amino-truncated and amino-elongated variants. Compounds have been identified which inhibit one or more of the AgrC receptors and more specifically which inhibit all four of the AgrC receptors at picomolar $IC_{50}$ values. Compounds which inhibit AgrC receptors also blocked hemolysis by wild-type *S. aureus* group I-IV strains. AgrC receptor inhibitors were also identified which attenuated the production of toxic shock syndrome toxin-1 (TSST-1), a QS phenotype in group III *S. aureus* infections. Compounds which exhibit group-selective inhibition of only one or two agr QS groups were also identified. Additionally, compounds which activate the AgrC-III receptor were identified.

The invention provides compounds of formula I:

and salts thereof where:

L is a divalent linker moiety 3 to 6 atoms in length;

Z is a divalent linker moiety 3 to 10 atoms in length;

$R_1$ and $R_2$ are independently selected from hydrogen, an optionally substituted alkyl group having 1-6 carbon atoms, an optionally substituted aryl group or an optionally substituted heteroaryl group;

$R_6$ and $R_7$ are independently selected from hydrogen, an optionally substituted alkyl group having 1-8 carbon atoms, an optionally substituted aryl group or an optionally substituted heteroaryl group; where, when $R_1$ is a group other than hydrogen or a methyl group, $R_6$ is a hydrogen or a methyl group and when $R_2$ is a group other than hydrogen or a methyl group, $R_7$ is a hydrogen or a methyl group;

$R_{10}$ is hydrogen or a methyl group; and $R_5$ is an optionally substituted alkyl group having 1-8 carbon atoms, an optionally substituted aryl group, an optionally substituted heteroaryl group or $R_5$ is:

$H_2N—CHR_{12}—$, $H_2N—CHR_{12}—CO—NR_{14}—$, $H_2N—CHR_{12}—CO—NR_{14}—CHR_{12}—$, $R_{15}—CO—NR_{14}—$, or $R_{15}—CO—NR_{14}—CHR_{12}—$, where each $R_{12}$ is hydrogen, an optionally substituted alkyl group having 1-6 carbon atoms, an optionally substituted aryl group or an optionally substituted heteroaryl group; $R_{14}$ is hydrogen, an optionally substituted alkyl group having 1-8 carbon atoms, an optionally substituted aryl group or an optionally substituted heteroaryl group; and $R_{15}$ is an optionally substituted alkyl group having 1-8 carbon atoms, an optionally substituted aryl group or an optionally substituted heteroaryl group where, when $R_5$ is $H_2N—CHR_{12}—CO—NR_{14}—$ and $R_{12}$ is a group other than hydrogen or a methyl, $R_{14}$ is hydrogen or a methyl group.

In specific embodiments, $R_5$ is an alkyl having 1-3 carbon atoms. In specific embodiments, $R_{12}$ is hydrogen, a methyl group or a $—CH_2—CO—NH_2$ group. In specific embodiments, $R_{14}$ is a methyl group. $R_{12}$ is hydrogen, a methyl group or a $—CH_2—CO—NH_2$ group and $R_{14}$ is methyl. In specific embodiments, $R_5$ is the dipeptidyl moiety A-A-, I-A-, A-N-, or I-NMeN.

The term "atoms in length" refers to the shortest number of atoms directly bonded between the points of attachment of L and Z in the formulas herein. If there are two or more possible ways to calculate the number of atoms bonded between the attachment points, the shortest number of atoms bonded between the two points is that which is intended to be limited by the recited range. For example, the linker $—CO—(CH_2)_5—CO—$ is 7 atoms in length (the =O atoms are not directly bonded between the points of attachment.

Compounds of the invention do not include the naturally occurring AIP-I, AIP-II, AIP-III or AIP-IV peptides. Compounds of the invention do not include tAIP-I D2A. In a specific embodiment, the compound of the invention is not the cyclic thioester (C-A-F-LL).

The invention also provides compounds of formula IA:

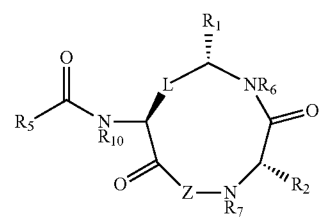

and salts thereof, where variable are as defined for formula I above.

In a specific embodiment, of formula I or IA, $R_6$ and $R_7$ are both H and $R_1$ and $R_2$ are alkyl groups having 3 to 6 carbon atoms. In a specific embodiment of formula IA, Z is 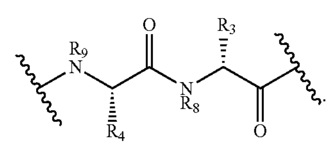 More specifically in this embodiment, $R_3$ is hydrogen, an optionally substituted alkyl group having 1-6 carbon atoms, an optionally substituted aryl group or an optionally substituted heteroaryl group; $R_4$ is hydrogen, or an optionally substituted alkyl group having 1-3 carbon atoms; and $R_9$ and $R_8$ are independently selected from hydrogen, an optionally substituted alkyl group having 1-8 carbon atoms, an optionally substituted aryl group or an optionally substituted heteroaryl group; wherein when $R_3$ is a group other than hydrogen or a methyl group, $R_8$ is a hydrogen or a methyl group and when $R_4$ is a group other than hydrogen or a methyl group, $R_9$ is a hydrogen or a methyl group. More specifically in this embodiment, $R_8$ and $R_9$ are both hydrogens. More specifically in this embodiment, $R_9$ is hydrogen or methyl and $R_4$ is hydrogen, methyl, or $—CH_2—COOH$. More specifically in this embodiment, $R_9$ is hydrogen, methyl or $—CH_2—COOH$ and $R_4$ is hydrogen or methyl. More specifically in this embodiment, $R_8$ is hydrogen or methyl and $R_3$ is hydrogen, an unsubstituted alkyl having 1-6 carbon atoms, a benzyl, a 4-OH benzyl, a (1H-indo-3-yl)methyl, or a (5-OH-1H-indo- 3-yl)methyl. More specifically in this embodiment, $R_8$ is an unsubstituted alkyl having 1-6 carbon atoms, a benzyl, a 4-OH benzyl, a (1H-indo-3-yl)methyl, or a (5-OH-1H-indo-3-yl)methyl, and $R_3$ is hydrogen or methyl. More specifically in this embodiment, $R_1$ and $R_2$ are independently alkyl groups having 2-6 carbon atoms and $R_6$ and $R_7$ are hydrogens.

The invention provides compounds of formula IIA:

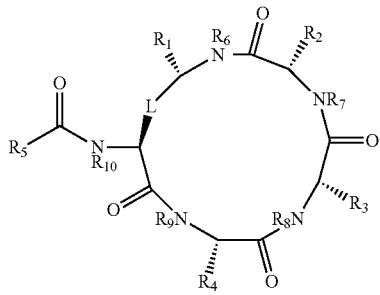

where L, $R_5$, and $R_{10}$ are as defined above;
$R_6$, $R_7$, $R_8$ and $R_9$ are independently selected from hydrogen or methyl;
$R_1$ and $R_2$ are selected from unsubstituted alkyl groups having 3-6 carbon atoms;
$R_4$ is an unsubstituted alkyl group having 1-3 carbon atoms; and
$R_3$ is an optionally substituted aryl group, an optionally substituted heterocyclic group or an alkyl having 1-3 carbon atoms substituted with an optionally substituted aryl or an optionally substituted heteroaryl or optionally substituted heterocyclic group, where substitution if present is substitution with one or more halogens, or —OH groups.

In specific embodiments of formula IIA, L is —$CH_2$—X—CO—, where X is S, N or O.

In specific embodiments of formula IIA, L is —$CH_2$—S—CO—.

In specific embodiments of formula IIA, $R_4$ is a methyl group.

In specific embodiments of formula IIA, $R_3$ is an alkyl having 1-3 carbon atoms substituted with an optionally substituted aryl or an optionally substituted heteroaryl or optionally substituted heterocyclic group.

In specific embodiments of formula IIA, $R_3$ is an unsubstituted alkyl having 1-6 carbon atoms, a benzyl, a 4-OH benzyl, a (1H-indo-3-yl)methyl, or a (5-OH-1H-indo-3-yl)methyl group.

The invention provides compounds of formula IIB:

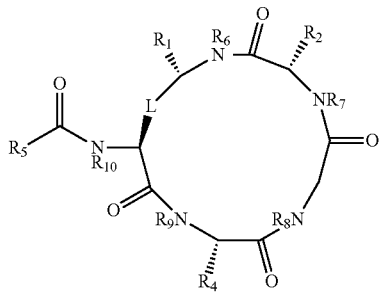

where L, $R_5$, and $R_{10}$ are as defined above for formulas I and IA;
$R_6$, $R_7$ and $R_9$ are independently selected from hydrogen or methyl;

$R_1$ and $R_2$ are selected from alkyl groups having 3-6 carbon atoms;
$R_4$ is an optionally substituted alkyl group having 1-3 carbon atoms, where substitution if present is substitution with one or more halogens, —OH, or —COON; and
$R_8$ is an optionally substituted aryl group, an optionally substituted heterocyclic group or an alkyl having 1-3 carbon atoms substituted with an optionally substituted aryl or an optionally substituted heteroaryl or optionally substituted heterocyclic group, where substitution, if present, is substitution with one or more halogens, or —OH groups.

In specific embodiments of formula IIA or IIB, $R_5$ is an alkyl having 1-3 carbon atoms. In specific embodiments, $R_{12}$ is hydrogen, a methyl group or a —$CH_2$—CO—$NH_2$ group. In specific embodiments, $R_{14}$ is a methyl group. $R_{12}$ is hydrogen, a methyl group or a —$CH_2$—CO—$NH_2$ group and $R_{14}$ is methyl. In specific embodiments, $R_5$ is the dipeptidyl moiety A-A-, I-A-, A-N-, or I-NMeN.

In specific embodiments of formula IIB, L is —$CH_2$—X—CO— where X is S, N or O.

In specific embodiments of formula IIB, L is —$CH_2$—S—CO—.

In specific embodiment of formula IIB, $R_8$ is an alkyl having 1-3 carbon atoms substituted with an optionally substituted aryl or an optionally substituted heteroaryl or optionally substituted heterocyclic group.

In a specific embodiment of formula IIB, $R_5$ is an alkyl group having 1-3 carbon atoms, $R_9$ and $R_4$ are independently hydrogen or methyl, and $R_3$ is an optionally substituted aryl or an optionally substituted heteroaryl and more specifically $R_3$ is benzyl, 4-OH-benzyl, or indoyl.

The invention provides compounds of formula III:

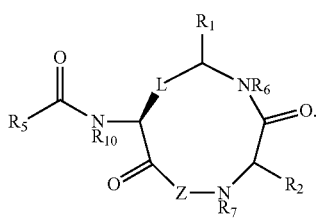

wherein $R_5$, $R_{10}$, L and Z are as defined as above; and
$R_1$, $R_2$, $R_6$ or $R_7$ selected from hydrogen or an alkyl group having 3-6 carbon atoms, wherein one or both of $R_7$ and $R_6$ are an alkyl group having 3-6 carbon atoms and if $R_6$ is an alkyl group, then $R_1$ is hydrogen and if $R_7$ is an alkyl group then $R_2$ is hydrogen.

In specific embodiments of formula III, L is —$CH_2$—S—CO—.

In specific embodiments of formula III, $R_6$ or $R_7$ is a 2-methyl propyl group.

In specific embodiments of formula III, Z is:
(i) a —$NR_9$—$(CH_2)_n$—CO— linker, where n is 1 to 7;
(ii) a —$NR_9$—$(CH_2)_n$—CO—$NR_8$—$CH(R_3)$—CO— linker; or
(ii) a —$NR_9$—$CH(R_4)$—CO—$NR_8$—$CH(R_3)$—CO— linker,
wherein $R_3$ is hydrogen, an optionally substituted alkyl group having 1-6 carbon atoms, an optionally substituted aryl group or an optionally substituted heteroaryl group;
$R_4$ is hydrogen, or an optionally substituted alkyl group having 1-3 carbon atoms; and $R_9$ and $R_8$ are independently selected from hydrogen, an optionally substituted alkyl group having 1-8 carbon atoms, an optionally substituted aryl group or an optionally substituted heteroaryl (or heterocyclic?) group; wherein when $R_3$ is a group other than hydrogen or a methyl group, $R_8$ is a hydrogen or a methyl group and when $R_4$ is a group other than hydrogen or a methyl group, $R_9$ is a hydrogen or a methyl group.

In specific embodiments of formula III, Z is —$NR_9$—CH($R_4$)—CO—$NR_8$—CH($R_3$)—CO—; where
$R_8$ and $R_9$ are hydrogen or methyl groups; and
$R_3$ is an alkyl group having 1-3 carbon atoms optionally substituted with an optionally substituted aryl, heterocyclic or heteroaryl group; an optionally substituted aryl group, an optionally substituted heteroaryl group or an optionally substituted heterocyclic group.

In specific embodiments of formula III, one or both of $R_1$ or $R_2$ is a 2-methylpropyl group; and $R_3$ is a methyl or ethyl group substituted with a phenyl, 5-OH-phenyl, a 1H-indo-3-yl or a 5-OH-1H-indo-3-yl group.

In specific embodiments of formula III, L is —$CH_2$—S—CO—; $R_3$ is a benzyl or a 4-OH benzyl group; and $R_4$ is a methyl or a —$CH_2$—COOH group.

In specific embodiments of formula III, $R_5$ is an alkyl having 1-3 carbon atoms. In specific embodiments, $R_{12}$ is hydrogen, a methyl group or a —$CH_2$—CO—$NH_2$ group. In specific embodiments, $R_{14}$ is a methyl group. $R_{12}$ is hydrogen, a methyl group or a —$CH_2$—CO—$NH_2$ group and $R_{14}$ is methyl. In specific embodiments, $R_5$ is the dipeptidyl moiety A-A-, I-A-, A-N-, or I-NMeN.

The invention provides compounds of formula IV and IVA:

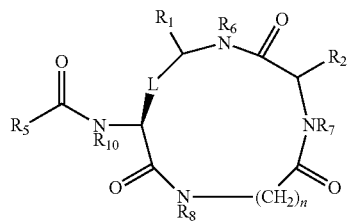

IV

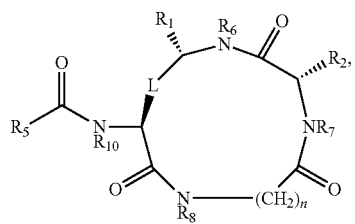

IVA where variables are as defined for formula I above and n is 1 to 7. In specific embodiments L is L is —$CH_2$—X—CO—, where X is S, O or NH. In more specific embodiments, L is —$CH_2$—S—CO—, or —$CH_2$—$CH_2$—S—CO—. In specific embodiments, $R_5$ is an alkyl group having 1-3 carbon atoms.

In specific embodiments of formula IV and IVA, n is 3, $R_6$-$R_8$ are hydrogen or methyl, $R_2$ is an alkyl having 1-6 or 4-6 carbon atoms, and $R_1$ is an alkyl group, particularly a methyl group substituted with an optionally substituted aryl, an optionally substituted heteroaryl, or an optionally substituted heterocyclic group. In more specific embodiments, $R_1$ is a methyl group substituted with an optionally substituted aryl group. In more specific embodiments, $R_1$ is a methyl group substituted with an optionally substituted phenyl group. In more specific embodiments, $R_1$ is a benzyl group. In specific embodiments $R_5$ is an alkyl group having 1-3 carbon atoms.

In specific embodiments of formula IV and IVA, n is 2, $R_6$-$R_8$ are hydrogen or methyl, $R_2$ is an alkyl having 1-6 or 4-6 carbon atoms, and $R_1$ is an alkyl group, particularly a methyl group substituted with an optionally substituted aryl, an optionally substituted heteroaryl, or an optionally substituted heterocyclic group. In more specific embodiments, $R_1$ is a methyl group substituted with an optionally substituted aryl group. In more specific embodiments, $R_1$ is a methyl group substituted with an optionally substituted phenyl group. In more specific embodiments, $R_1$ is a benzyl group. In specific embodiments $R_5$ is an alkyl group having 1-3 carbon atoms.

In specific embodiments of formula IV and IVA, n is 5-7, $R_6$-$R_8$ are hydrogen or methyl, $R_2$ is an alkyl having 1-6 or 4-6 carbon atoms, and $R_1$ is an alkyl group, particularly a methyl group substituted with an optionally substituted aryl, an optionally substituted heteroaryl, or an optionally substituted heterocyclic group. In more specific embodiments, $R_1$ is a methyl group substituted with an optionally substituted aryl group. In more specific embodiments, $R_1$ is a methyl group substituted with an optionally substituted phenyl group. In more specific embodiments, $R_1$ is a benzyl group. In specific embodiments $R_5$ is an alkyl group having 1-3 carbon atoms.

In specific embodiments of any formulas herein, $R_5$ is an alkyl group having 1-3 carbon atoms which is substituted with an optionally substituted carbocyclic or heterocyclic group. In a specific embodiment, the carbocyclic or heterocyclic group has a 5- or 6-member ring which is saturated or unsaturated and in which one or two ring carbons are —CO— moieties. In a specific embodiment, $R_5$ is:

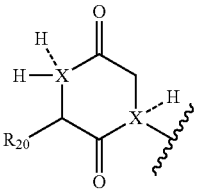

where X is carbon or nitrogen and if X is carbon an additional hydrogen is present to satisfy valence; and R20 is an optionally substituted alkyl group having 1-6 carbon atoms where optionally substitution is substitution with one or more hydroxyl, halogen, alkoxy, amino, alkylamino or dialkylamino groups.

In specific embodiments of any formula herein, $R_5$ is the dipeptidyl moiety A-A-, I-A-, A-N-, or I-NMeN.

In specific embodiments of any formula herein, $R_9$ is hydrogen or methyl and $R_4$ is hydrogen, methyl, or —$CH_2$—COOH. In specific embodiments of any formula herein, $R_9$ is hydrogen, methyl or —$CH_2$—COOH and $R_4$ is hydrogen or methyl. In specific embodiments of any formula herein, $R_8$ is hydrogen or methyl and $R_3$ is hydrogen, an unsubstituted alkyl having 1-6 carbon atoms, a benzyl, a 4-OH benzyl, a (1H-indo-3-yl)methyl, or a (5-OH-1H-indo-3-yl)methyl. In specific embodiments of any formula herein, $R_8$ is an unsubstituted alkyl having 1-6 carbon atoms, a benzyl, a 4-OH benzyl, a (1H-indo-3-yl)methyl, or a (5-OH-1H-indo-3-yl) methyl, and $R_3$ is hydrogen or methyl. In specific embodiments of any formula herein, $R_1$ and $R_2$ are independently alkyl groups having 2-6 carbon atoms and $R_6$ and $R_7$ are hydrogens.

The terms alkyl or alkyl group refer to a monoradical of a straight-chain or branched saturated hydrocarbon. Alkyl groups include straight-chain and branched alkyl groups. Unless otherwise indicated alkyl groups have 1-8 carbon atoms (C1-C8 alkyl groups) and preferred are those that contain 1-6 carbon atoms (C1-C6 alkyl groups) and more preferred are those that contain 1-3 carbon atoms (C1-C3 alkyl groups). Alkyl groups are optionally substituted with one or more non-hydrogen substituents as described herein. Exemplary alkyl groups include methyl, ethyl, n-propyl, iso-propyl, cyclopropyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

Cycloalkyl groups herein preferably have 1 ring having 5-8 carbon atoms and preferably have 5 or 6 carbon atoms. Cycloalkylene refers to divalent moieties derived formally from cycloalkyl groups as described above by removal of an additional hydrogen e.g., —($C_6H_{12}$)—, a cyclohexenyl. Cycloalkylene, particularly cyclohexylene groups are often employed in linkers.

An carbocyclic group is a group having one or more saturated or unsaturated carbon rings. Carbocyclic groups, for example, contain one or two double bonds. One or more carbons in an carbocyclic ring can be —CO— groups. carbocyclic c groups include those having 3-12 carbon atoms, and optionally replacing 1 or 2 carbon atoms with a —CO— group and optionally having 1, 2 or 3 double bonds. Carbocyclic groups include those having 5-6 ring carbons. Carbocyclic groups can contain one or more rings each of which is saturated or unsaturated. Carbocyclic groups include bicyclic and tricyclic groups. Preferred carbocyclic groups have a single 5- or 6-member ring. Carbocyclic groups are optionally substituted as described herein. Specifically, carbocyclic groups can be substituted with one or more alkyl groups. Carbocyclic groups include among others cycloalkyl and cycloalkenyl groups.

A heterocyclic group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclic groups include those having 3-12 carbon atoms, and 1-6, heteroatoms, wherein 1 or 2 carbon atoms are replaced with a —CO— group. Heterocyclic groups include those having 3-12 or 3-10 ring atoms of which up to three can be heteroatoms other than carbon. Heterocyclic groups can contain one or more rings each of which is saturated or unsaturated. Heterocyclic groups include bicyclic and tricyclic groups. Preferred Heterocyclic groups have 5- or 6-member rings. Heterocyclic groups are optionally substituted as described herein. Specifically, heterocyclic groups can be substituted with one or more alkyl groups. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic group include those having 5- or 6-member rings and two different heteroatom, e.g., N and O, O and S or N and S. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Heterocyclene refers to a divalent species formally derived from a heterocylic group as described above by removal of a hydrogen.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, and purinyl groups. In specific embodiments herein aryl groups contain no heteroatoms in the aryl rings. Aryl including heteroaryl groups are optionally substituted.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

Arylalkyl groups are alkyl groups substituted with one or more aryl groups wherein the alkyl groups optionally carry additional substituents and the aryl groups are optionally substituted. Exemplary arylalkyl groups are benzyl groups.

Heteroarylalkyl groups are alkyl groups substituted with one or more heteroaryl groups wherein the alkyl groups optionally carry additional substituents and the aryl groups are optionally substituted.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

Alkylheteroaryl groups are heteroaryl groups substituted with one or more alkyl groups wherein the alkyl groups optionally carry additional substituents and the aryl groups are optionally substituted.

An alkoxy group is an alkyl group, as broadly discussed above, linked to oxygen ($R_{alkyl}$-O—). An aryloxy group is an aryl group, as discussed above, linked to an oxygen ($R_{aryl}$-O—). A heteroaryloxy group is a heteroaryl group as discussed above linked to an oxygen ($R_{heteroaryl}$-O—)

An acyl group is an R'—CO group where R' in general is a hydrogen, an alkyl, alkenyl or alkynyl, aryl or heteroaryl group as described above. In specific embodiments, acyl groups have 1-20, 1-12 or 1-6 carbon atoms and optionally 1-3 heteroatom, optionally one double bond or one triple bond. In specific embodiments, R is a C1-C6 alkyl, alkenyl or alkynyl group. cyclic configuration or a combination thereof, attached to the parent structure through a carbonyl functionality. Examples include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

An alkylthio group is an alkyl group, as broadly discussed above, linked to a sulfur ($R_{alkyl}$—S—) An arylthio group is an aryl group, as discussed above, linked to a sulfur ($R_{aryl}$-S—).

The term amino group is refer to the species —N(H)$_2$—. The term alkylamino refers to the species —NHR" where R" is an alkyl group, particularly an alkyl group having 1-3 carbon atoms. The term dialkylamino refers to the species —NR"$_2$ where each R" is independently an alkyl group, particularly an alkyl group having 1-3 carbon atoms.

Groups herein are optionally substituted most generally alky, alkenyl, alkynyl, and aryl, heteroaryl groups can be substituted with one or more halogen, hydroxyl group, nitro group, cyano group, isocyano group, oxo group, thioxo group, azide group, cyanate group, isocyanate group, acyl group, haloakyl group, alkyl group, alkenyl group or alkynyl group (particularly those having 1-4 carbons), a phenyl or benzyl group (including those that are halogen or alkyl substituted), alkoxy, alkylthio, or mercapto (HS—). In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxy group, cyano group, oxo group, thioxo group, unsubstituted C1-C6 alkyl group or unsubstituted aryl group. The term oxo group and thioxo group refer to substitution of a carbon atom with a =O or a =S to form respectively —CO— (carbonyl) or —CS— (thiocarbonyl) groups.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention, particularly compounds of formulas I, IA, IIA, IIB, III, IV and IVA can be prepared by one of ordinary skill in the art in view of the descriptions provided herein and what is known in the art from commercially or otherwise readily available starting materials and reagents. As described herein in the Examples, standard solid-phase methods of peptide synthesis can be readily adapted for synthesis of the compounds of the formulas herein. Methods for insertion of peptoids, and N-methylated amino acids into such compounds are known in the art and can, as described herein, be readily adapted to such preparation. Among others references [67], [70], and [75]-[80] provide methods useful in synthesis of the compounds herein. Each of these references is incorporated by reference herein in its entirety for description of such methods.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings*, Adv. Drug Del. Rev., 2001, 46, 3-26 and Arup K. Chose, Vellarkad N. Viswanadhan, and John J. Wendoloski, *A Knowledge-Based Approach in Designing Combinatorial or Medicinal Chemistry Libraries for Drug Discovery*, J. Combin. Chem., 1999, 1, 55-68.) In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; and (4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Salt of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

The invention expressly includes pharmaceutically usable solvates of compounds according to formulas herein. The compounds of formula I can be solvated, e.g. hydrated. The solvation can occur in the course of the manufacturing process or can take place, e.g. as a consequence of hygroscopic properties of an initially anhydrous compound of formulas herein (hydration).

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Staphylococcal infections, particularly *S. aureus* infections, can affect various parts of the body and can include skin infection and more serious conditions such as osteomyelitis, endocarditis, septic arthritis, and toxic shock syndrome. *S. aureus* strains are considered the leading cause of nosocomial infections in the United States. Staphylococcal infections, particularly *S. aureus* infections, caused by a strain that is resistant to commonly used antibiotics are particularly serious and life-threatening. Of particular concern are strains that exhibit increased resistance to vancomycin.

Compounds of the invention are useful in the treatment of such infections. Administration of one or more compounds of the invention can be combined with antibiotic regimens used for the treatment of staphylococcal infections. Various known antibiotics and various known antibiotic regimens can be employed in combination with one or more of the compounds of this invention. One of ordinary skill in the art can select form a variety of known antibiotics, which may be used alone or in combination, and which can specifically include, vancomycin, linezolid, and oxacillin. For example, one or more compounds of the invention can be used in combination with intravenous or oral antibiotics.

In another embodiment, the invention provides a medicament for treatment of an infectious disease, particularly a staphylococcal infection. The medicament comprises a therapeutically effective amount of one or more compounds of this invention as illustrated in one or more formulas herein which compounds exhibit antivirulence and/or antibacterial activity. In a specific embodiment, the medicament of this invention can also comprise a therapeutically effective amount of one or more antibiotics. The invention also provides a method for making this medicament which comprises combining a therapeutically effective amount of one or more compounds of this invention having anti-virulence activity with a selected pharmaceutical carrier appropriate for a given method of administration. In a specific embodiment, the method for making a medicament can additional include combining a therapeutically effective amount of one or more antibiotics in the medicament. The medicament may be an oral dosage form, an intravenous dosage form or any other art-recognized dosage form.

The present invention also provides methods of increasing or reducing the virulence of *Staphylococcus* species and specifically *Staphylococcus aureus*. In one aspect, the method comprises contacting a bacterium with an effective amount of a compound of the present invention. In another aspect, the method comprises contacting a bacterium with a therapeutically effective amount of a pharmaceutically acceptable salt of the compounds of the present invention. In yet another aspect, the method comprises contacting a bacterium with a precursor which can form an effective amount of a compound of the present invention.

Methods of this invention comprise the step of administering a "therapeutically effective amount" of the present therapeutic formulations containing the present compounds, to treat, reduce or regulate a disease state in a patient, including a disease state involving one or more infectious agents such as bacteria. The term "therapeutically effective amount," as used herein, refers to the amount of the therapeutic formulation, that, when administered to the individual is effective to treat, reduce or regulate a disease state in a patient, including a disease state involving one or more infectious agents such as bacteria and more specifically *Staphylococcus*. As is understood in the art, the therapeutically effective amount of a given compound or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound can be determined as is understood in the art.

Compounds of the invention are useful in therapeutic methods, particularly for treating infections. Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds of this invention can also be administered to the eye, preferably as a topical opthalmic formulation. The compounds of this invention can also be combined with a preservative and an appropriate vehicle such as mineral oil or liquid lanolin to provide an opthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non-toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety. The invention also encompasses method for making a medicament employing one or more compounds of this invention which exhibit a therapeutic effect.

In another aspect, the present invention provides pharmaceutical and therapeutic preparations comprising a therapeutically effective amount of one or more compounds of the present invention of Formula I optionally in combination with a pharmaceutically acceptable carrier. In particular, pharmaceutical and therapeutic preparations of this invention comprise an amount or combined amount of one or more compounds of this invention effective for bacterial interference, particularly of a *Staphylococcus* species and more particularly of *Staphylococcus aureus* and including a *Staphylococcus aureus* group III strain and more particularly a bacterial human or veterinary pathogen. Compounds useful in the methods of this invention include pharmaceutically-acceptable salts of the compounds of formulas herein. Compounds useful in the methods of this invention include pharmaceutically-acceptable prodrugs of the compounds of formulas herein. Salts include any salts derived from the acids of the formulas herein which are acceptable for use in human or veterinary applications. Bacterial interference includes attenuation of virulence.

In another aspect, the present invention provides a method of treating an infectious disease comprising administering to an individual in need of treatment, a composition comprising one or more compounds of the present invention. In an embodiment, the infectious disease relates to that associated with an infectious agent comprising a bacterium. In a specific embodiment, the bacteria are *Staphylococcus*. In a specific embodiment, the bacteria are one or more selected from the group consisting of *S. aureus, S. epidermidis*. In a specific embodiment, the bacteria are one or more drug resistant *Staphylococcus*. Compounds of the invention can be employed in human treatment or in veterinary treatment. All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Synthetic Methods

Linear peptides were synthesized on Boc-protected, amino acid pre-loaded 4-hydroxymethyl-phenylacetamidomethyl (PAM) resin (0.6-0.8 mmol/g) using standard solid-phase synthesis protocols.

All chemical reagents were purchased from commercial sources (Alfa-Aesar, Sigma-Aldrich, and Acros) and used without further purification. Solvents were purchased from commercial sources (Sigma-Aldrich and J. T. Baker) and used as obtained, with the exception of anhydrous dichloromethane ($CH_2Cl_2$), which was stored over molecular sieves. Water (18 M$\Omega$) was purified using a Millipore Analyzer Feed System. Solid-phase resin was purchased from Chem-Impex International. Cyclic dipeptides (cyclo-(Tyr- Pro) and cyclo-(Phe-Pro)) controls were synthesized according to a previously reported method.[57]

Reversed-phase high performance liquid chromatography (RP-HPLC) was performed using a Shimadzu system equipped with an SCL-10Avp controller, an LC-10AT pump, an FCV-10ALvp solvent mixer, and an SPD-10MAvp UV/vis diode array detector. An analytical Phenomenex Gemini C18 column (5 µm, 4.6 mm×250 mm, 110 Å) was used for analytical RP-HPLC work. A semi-preparative Phenomenex Gemini C18 column (5 Åm, 10 mm×250 mm, 110 Å) was used for preparative RP-HPLC work. Standard RP-HPLC conditions were as follows: flow rates=1 mL min$^{-1}$ for analytical separations and 5 mL min$^{-1}$ for semi-preparative separations; mobile phase A=18 MΩ water+0.1% trifluoroacetic acid (TFA); mobile phase B=acetonitrile (ACN)+0.1% TFA. Purities were determined by integration of peaks with UV detection at 220 nm. Peptide thioesters were purified using a linear gradient (75%→45% A over 30 min). Cyclic peptides were purified using a linear gradient (70%→55% A over 27 min). Overall sample purity was determined using a linear gradient (90%→5% A over 27 min). MALDITOF mass spectrometry (MS) data were obtained on a Bruker RELEX II spectrometer equipped with a 337 nm laser and a reflectron. In positive ion mode, the acceleration voltage was 25 kV. Exact Mass (EM) data were obtained on a Waters (Micromass) LCT ESI-TOF spectrometer. The samples were sprayed with a sample cone voltage of 20 V.

Peptide Synthesis.

Two solid-phase synthesis approaches have been implemented in the past to construct native AIPs and their analogs. The first approach utilizes chemoselective cleavage of the linear, protected peptide from the solid support with concomitant unmasking of the cysteine sulfhydryl group. The protected peptide can then be macrocyclized via a carbodiimide coupling and subsequently deprotected. [24, 50, 61] This approach, however, is limited in part by the (i) poor solubilities of the protected peptides and (ii) low macrocyclization efficiencies due to the steric bulk of the protecting groups. The second synthetic approach addresses these challenges by incorporating an initial global deprotection step prior to a solution phase, chemoselective thiol-thioester exchange to form the macrocyclic products.[45, 49] This latter approach is generally more efficient and has the potential for even further improvement. This general strategy was used to synthesize compounds of Table 1 herein. First, standard Fmoc/tBu solid-phase peptide synthesis methods to generate the linear peptides on 4-hydroxymethyl-phenylacetamido methyl (PAM) polystyrene resin (Scheme 1). Cleavage and global deprotection according to the method of Hilvert et al. gave the linear peptide thioesters,[51, 62, 63] which were then purified to homogeneity by semi-preparative RP-HPLC and isolated in acceptable yields (25-50%).

Scheme 1: Solid phase synthetic route to AIPs and analogs.

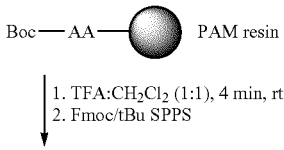

1. TFA:CH$_2$Cl$_2$ (1:1), 4 min, rt
2. Fmoc/tBu SPPS

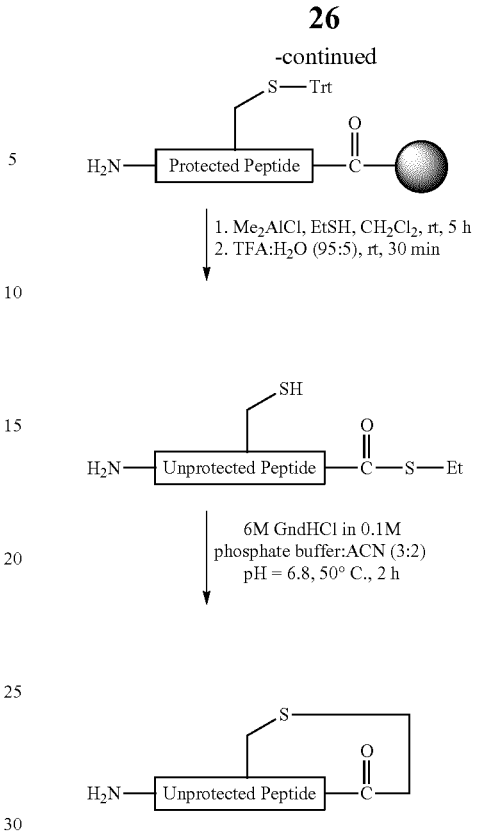

TFA = trifluoroacetic acid; SPPS = solid-phase peptide synthesis; GndHCl = guanidinium chloride.

Intramolecular thiol-thioester exchange reactions in a range of buffers was assessed to Studies were then undertaken to develop macrocyclization conditions. It was found that found that performing the macrocyclization reaction in 6 M guanidinium chloride in 0.1 M phosphate buffer:ACN (3:2, vol:vol) at a pH=6.8 gave quantitative macrocyclization within 24 h at room temperature. Elevating the 50° C. reduced reaction times to less than 2 h. These conditions were used to effect macrocyclization of all the AIP analogs prepared in this study (Table 1). This synthesis protocol was also used to generate AIPs I-IV and the known global AgrC inhibitor, tAIP-I D2A, for use as controls. Overall, this synthetic route represents an improvement over previously reported methods.[45, 49, 51] Further, the thiol-thioester exchange reaction conditions described herein can also be used in other contexts, for example, in the total synthesis of proteins using native chemical ligation. [64] Dawson et al. (1994) [64] is incorporated by reference herein in its entirety for a description of the synthesis of polypeptides by native chemical ligation.

These synthetic methods were employed to prepare the compounds of Table 1. Initially a set of 13 compounds were prepared in which the amino acids of AIP-III were evaluated through systematic alanine and D-amino acid point mutations. This initial set of 13 peptides (Table 1) was designed to identify key residues and stereocenters for AIP-III:AgrC interactions. Six of the seven residues were modified in the alanine scan with Cys3 maintained for thiolactone formation. All seven residues were evaluated in the D-amino acid scan. A second set of compounds was synthesized to include two and three alanines, alternate aromatic residues in place of Phe5, and to truncate and elongate exocyclic tails.

TABLE 1

Structures of the peptides synthesized in this study.[a]

| Peptide name | Sequence |
|---|---|
| AIP-I | Y-S-T-(C-D-F-I-M) |
| AIP-II | G-V-N-A-(C-S-S-L-F) |
| tAIP-I D2A | Ac-(C-A-F-I-M) |
| AIP-III | I-N-(C-D-F-L-L) |
| AIP-IV | Y-S-T(C-Y-F-I-M) |

| 1st Generation analogues | | 2nd Generation analogues | |
|---|---|---|---|
| AIP-III D-I1 | DI-N-(C-D-F-L-L) | AIP-III I1A/N2A | A-A-(C-D-F-L-L) |
| AIP-III D-N2 | I-DN-(C-D-F-L-L) | AIP-III I1A/D4A | A-N-(C-A-F-L-L) |
| AIP-III D-C3 | I-N-(DC-D-F-L-L) | AIP-III N2A/D4A | I-A-(C-A-F-L-L) |
| AIP-III D-D4 | I-N-(C-DD-F-L-L) | AIP-III | A-A-(C-A-F-L-L) |
| | | I1A/N2A/D4A | |
| AIP-III D-F5 | I-N-(C-D-DF-L-L) | tAIP-III | Ac-(C-D-F-L-L) |
| AIP-III D-L6 | I-N-(C-D-F-DL-L) | tAIP-III D2A | Ac-(C-A-F-L-L) |
| AIP-III D-L7 | I-N-(C-D-F-L-DL) | tAIP-III D2A/F3Y | Ac-(C-A-Y-L-L) |
| AIP-III I1A | A-N-(C-D-F-L-L) | tAIP-III D2A/F3W | Ac-(C-A-W-L-L) |
| AIP-III N2A | I-A-(C-D-F-L-L) | Ac-AIP-III | Ac-I-N-(C-D-F-L-L) |
| AIP-III D4A | I-N-(C-A-F-L-L) | G-AIP-III | G-I-N-(C-D-F-L-L) |
| AIP-III F5A | I-N-(C-D-A-L-L) | A-AIP-III | A-I-N-(C-D-F-L-L) |
| AIP-III L6A | I-N-(C-D-F-A-L) | Y-AIP-III | Y-I-N-(C-D-F-L-L) |
| AIP-III L7A | I-N-(C-D-F-L-A) | | |

[a]See Supporting information for MS and HPLC characterization data. Shaded cells represent control peptides.

Representative Peptide Synthesis

To deprotect the resin, a portion of resin (50 mg) was first swelled by suspension in $CH_2Cl_2$ (2 mL) for 30 min at rt and then drained. The resin was then treated with TFA (50% in $CH_2Cl_2$, 2 mL, 2×2 min, rt) and washed with dimethylformamide (DMF; 3×2 mL). To couple each amino acid, Fmoc-protected amino acids (2 equiv. relative to resin), 2-(1Hbenzotriazole-1-yl)-1,1,3,3-tetramethyluronium hexafluorophosphate (HBTU; 2 equiv.), and diisopropylethylamine (DIPEA; 2 equiv.) were dissolved in DMF (2 mL). The solution was allowed to pre-activate for 1 min prior to being added to the resin and agitated for 1 h at rt. After each coupling step, the resin was drained and washed with DMF (2×2 mL). To remove the Fmoc-protecting group after each coupling, the resin was treated with piperidine (2 mL of 20% in DMF, 2×10 min) and washed with DMF (3×2 mL). To acetylate the amino terminus, acetic anhydride (10 equiv.) and DIPEA (7 equiv.) were dissolved in DMF (2 mL), and the solution was added to the resin and agitated for 15 min. The resin was then drained and washed with DMF (2×2 mL). Upon synthesis of a complete linear peptide sequence, the resin was washed with diethyl ether (1×2 mL) and dried under vacuum for 48 h.

Peptide Cleavage Protocol

The linear peptidyl-resin (70-90 mg) was placed in a dry, three-neck round bottom flask and suspended in anhydrous $CH_2Cl_2$ under argon at rt for 15 min. $Me_2AlCl$ (20 equiv., 1 mL of 1 M hexane solution) and anhydrous $CH_2Cl_2$ (3 mL) were stirred in a separate, dry round bottom flask under argon for 5 min at 0° C. Ethanethiol (EtSH) (60 equiv.) was added drop-wise at 0° C., and the solution was stirred for 15 min at 0° C. This solution was then added to the suspended resin and stirred under argon for 5 h at rt to effect cleavage of the linear peptide as a thioester. The cleavage product solution was transferred into a new round bottom flask containing a TFA solution (95% (aq.), 3 mL) and the solvents were removed in vacuuo to yield a yellow or orange oil. The resulting oil was subjected again to TFA solution (3 mL, 30 min) and filtered from the resin. The resin was washed with TFA solution (1×2 mL) to collect any additional peptide. A cooled solution of diethyl ether:hexane (1:1, 40 mL, 0° C.) was added to the filtrate, and the peptide was allowed to precipitate overnight in a freezer at −20° C. The precipitated peptide solution was centrifuged and the supernatant removed to yield a white solid. This solid was dissolved in acetonitrile (ACN) (50% (aq.)), lyophilized, redissolved in ACN (50% (aq.)) and purified by semi-preparative RP-HPLC. Collected HPLC fractions were lyophilized to yield the linear peptide thioester as a white powder (25-50% isolated yields).

Representative Peptide Macrocyclization Protocol

Purified peptide thioester was dissolved in a 60% guanidinium chloride (6 M solution in 0.1 M phosphate buffer): 40% ACN solution to a final concentration ranging from 100 μM to 2 mM. The pH of the solution was then adjusted to 6.8. The peptide was gently agitated using a multi-purpose rotator at 50° C. and cyclization was monitored by analytical RP-HPLC. Upon completion, cyclic peptide was purified by semi-preparative RP-HPLC and lyophilized. The resulting white powder was then dissolved in 1Mhydrochloric acid (400 μL) and lyophilized prior to bioanalysis.

Example 2

Peptidomimetics

Two sets of peptidomimetics, resulting from an N-methyl scan and a peptoid scan of AIP-III, were prepared to assess backbone-amide hydrogen bond interactions and conformational restrictions of the AIP-III scaffold. These peptidomimetics are illustrated in FIG. 4. The method of Example 1 involving initial synthesis of linear peptidyl thioesters using Fmoc peptide assembly on PAM resin followed by chemoselective cyclization was not suitable for the synthesis of peptides containing N-alkylated amino acids at the C-terminus. It is well-known that a side reaction, diketopiperazine (DKP) formation, is observed for C-terminal proline-containing peptides and N-methylated peptides.[51, 76, 77] To circumvent this side reaction and minimize DKP formation, the linear peptidomimetic thioesters were synthesized in a Boc/Fmoc hybrid peptide assembly: the three C-terminal residues (Phe-Leu-Leu) were introduced using Boc chemistry and the four N-terminal residues (Ile-Asn-Cys-Asp) were introduced using Fmoc chemistry (Scheme 2). To introduce peptoid residues, a sub-monomer protocol was used, [75] while commercially-available N-methylated amino acids were introduced through standard protocols. Zuckermann et al. 1992 [75] is incorporated by reference herein in its entirety for methods of synthesis of compounds of this invention. This hybrid synthetic route provided all of the compounds of FIG. 4 in acceptable yields, with the exception of AIP-III nN2 that was found to further react in aqueous solutions. All products were purified to homogeneity by RP-HPLC and obtained in ~mg scale.

Scheme 2: Synthetic route for peptidomimetics;

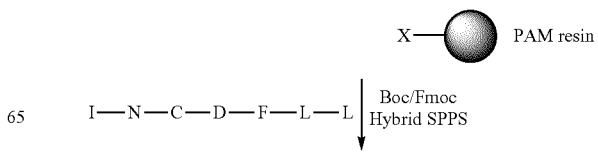

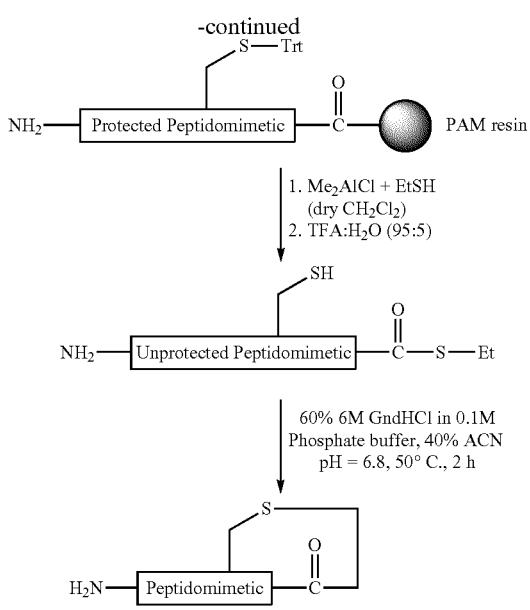

TFA = trifluoroacetic acid; SPPS = solid-phase peptide synthesis; GndHCl = guanidinium chloride.

Synthetic Methods

Peptidomimetic AIP-III derivatives that were not modified at the C-terminus residue (Leu7) were synthesized using Boc-protected, L-leucine pre-loaded PAM resin (0.8 mmol/g).

To synthesize the AIP-III N-Me-L7 derivative, Fmoc-N-Me-Leu-OH was manually loaded on aminomethyl polystyrene (AM) resin: AM resin (100 mg, 1.17 mmol/g) was swelled in diisopropylethylamine (DIPEA; 10% in CH$_2$Cl$_2$; 2 mL) for 10 min. The resin was washed with DIPEA (10% in CH$_2$Cl$_2$; 3×1 mL) and dimethylformamide (DMF; 3×2 mL). 4-(bromomethyl) phenyl acetic acid (1.4 equiv.) and N,N'-diisopropylcarbodiimide (DIC; 1.7 equiv.) were dissolved in CH$_2$Cl$_2$. The solution was added to the resin for overnight agitation at rt. The resin was washed with DMF (3×2 mL) and CH$_2$Cl$_2$ (3×2 mL), then suspended in DMF. Fmoc-N-Me-Leu-OH (2 equiv.) and DIPEA (4 equiv.) were dissolved in DMF and added to the resin for overnight agitation at rt. The resin was washed with DMF (2×2 mL) and CH$_2$Cl$_2$ (2×2 mL), then treated with a solution of acetic anhydride (10 equiv.) and DIPEA (7 equiv.) in DMF for 15 min. The resin was then washed with DMF (2×2 mL) and CH$_2$Cl$_2$ (2×2 mL), followed by chloranil test to determine the absence of free amines (see procedure below).

To synthesize the AIP-III nL7 analog, bromoacetic acid was manually loaded on PAM resin: PAM resin (100 mg, 0.85 mmol/g) was swelled in minimal amount of DMF (1 mL) for 30 min. Bromoacetic acid (10 equiv.) was dissolved in dry CH$_2$Cl$_2$ at 0° C. DIC (5 equiv.) was added, the reaction was stirred at 0° C. for 20 min and the solvent was removed in vacuo. The resulting solid was dissolved in minimal amount of DMF (1 mL) and 4-dimethylaminopyridine (DMAP; 0.1 equiv.) was added. The solution was added to the resin and agitated for 1 h at rt. The solvent was drained and the resin was washed with DMF (2×2 mL) and CH$_2$Cl$_2$ (2×2 mL).

To swell the resins: the resin (50 mg) was first suspended in CH$_2$Cl$_2$ (2 mL) for 30 min at rt and then drained.

To remove the Boc-protecting group: the resin was treated with TFA (50% in CH$_2$Cl$_2$, 2 mL, 2×2 min, rt) and washed with DMF (3×2 mL). To couple each amino acid after Boc removal: the standard in situ neutralization/activation protocol was used. [78] Boc/Fmoc-protected amino acids (4 equiv.), 2-(1H-benzotriazole-1-yl)-1,1,3,3-tetramethyluronium hexafluorophosphate (HBTU; 4 equiv.), and DIPEA (6 equiv.) were dissolved in DMF (2 mL). The solution was allowed to pre-activate for 2 min prior to being added to the resin and agitated for 30 min at rt. After each coupling step, the resin was drained and washed with DMF (2×2 mL).

To remove the Fmoc-protecting group: the resin was treated with piperidine (2 mL of 20% in DMF, 2×10 min) and washed with DMF (3×2 mL). To couple each amino acid after Fmoc removal: Boc/Fmoc-protected amino acids (2 equiv.), HBTU (2 equiv.), and DIPEA (2 equiv.) were dissolved in DMF (2 mL). The solution was allowed to pre-activate for 1 min prior to being added to the resin and agitated for 1 h at rt.

To couple bromoacetic acid:bromoacetic acid (10 equiv.) was dissolved in DMF (2 mL). DIC (10 equiv.) was added and the solution was pre-activated for 20 min. The solution was added to the resin and the reaction was agitated for 30 min. The resin was drained and the procedure was repeated. The resin was washed with DMF (2×2 mL) and CH$_2$Cl$_2$ (2×2 mL), followed by chloranil test to determine the reaction completion (see procedure below). To couple primary amines to the bromoacetic acid: the amine (10 equiv.) was dissolved in DMF (2 mL). DIPEA (10 equiv.) was added and the solution was allowed to pre-activate for 1 min prior to being added to the resin and agitated overnight using a multi-purpose rotator at 50° C. The resin was washed with DMF (2×2 mL) and CH$_2$Cl$_2$ (2×2 mL), followed by chloranil test to determine the presence of free amines (see procedure below).

To couple amino acids to secondary amines: Boc/Fmoc-protected amino acids (4 equiv.), 2-(7-Aza-1H-benzotriazole-1-yl)-1,1,3,3-tetramethyluronium hexafluorophosphate (HATU; 4 equiv.), and DIPEA (4 equiv.) were dissolved in DMF (2 mL). The solution was allowed to pre-activate for 1 min prior to being added to the resin and agitated for 2 h at rt. The resin was washed with DMF (2×2 mL) and CH$_2$Cl$_2$ (2×2 mL), followed by chloranil test to determine the reaction completion (see procedure below). If the test indicated that free amines are still present, the procedure was repeated and the reaction was left overnight at 50° C. After the second coupling cycle, peptide elongation was continued even if the chloranil test indicated that free amines are still present.

To carry out the chloranil test: A sample containing 1-3 mg of the resin was withdrawn and placed into a test tube. Acetaldehyde (2% in DMF; 2 drops) and chloranil (2% in toluene; 2 drops) were added to the sample. The solution was agitated at rt for 5 min. A green or blue color of the beads is a positive indication for the presence of free amines, indicating deprotection of the protecting group or incomplete coupling reaction.

PAM Resin Cleavage Protocol

Upon synthesis of a complete linear peptide sequence, the resin was washed with diethyl ether (1×2 mL) and dried under vacuum for 48 h. The linear peptidyl-resin (90 mg) was placed in a dry, three-neck round bottom flask and suspended in anhydrous CH$_2$Cl$_2$ under argon at rt for 15 min. Me$_2$AlCl (20 equiv., 1 mL of 1 M hexane solution) and anhydrous CH$_2$Cl$_2$ (3 mL) were stirred in a separate, dry round bottom flask under argon for 5 min at 0° C. Ethanethiol (EtSH) (60 equiv.) was added drop-wise at 0° C., and the solution was stirred for 15 min at 0° C. This solution was then added to the suspended resin and stirred under argon for 5 h at rt to effect cleavage of the linear peptide as a thioester. The cleavage product solution was transferred into a new round bottom flask containing a TFA solution (95% (aq.), 3 mL) and the solvents were removed in vacuo to yield a yellow or orange oil. The resulting oil was subjected again to TFA solution (3 mL, 30 min) and filtered from the resin. The resin was washed with TFA solution (1×2 mL) to collect any additional peptide. A cooled solution of diethyl ether:hexane (1:1, 40 mL, 0° C.) was added to the filtrate, and the peptide was allowed to precipitate overnight in a freezer at −20° C. The precipitated peptide solution was centrifuged and the supernatant removed to yield a white solid. This solid was dissolved in ACN (50% (aq.)), lyophilized, redissolved in ACN (50% (aq.)) and purified by semi-preparative RP-HPLC. Collected HPLC fractions were lyophilized to yield the peptide thioester as a white powder (5-20% isolated yields).

Peptide Cyclization Protocol

Purified peptidomimetic thioester was dissolved in a 60% guanidinium chloride (6 M solution in 0.1 M phosphate buffer):40% ACN solution to a final concentration ranging from 100 μM to 2 mM. The pH of the solution was then adjusted to 6.8. The peptide was agitated using a multi-purpose rotator at 50° C. for 2 h. The cyclic peptide was purified by semi-preparative RP-HPLC and lyophilized. The resulting white powder was then dissolved in 1M hydrochloric acid (400 μL) and lyophilized.

AIP-III nN2

The AIP-III nN2 thioester reacted immediately after purification to quantitatively generate an alternative product 17 mass units lower than expected. MS/MS analysis of the final product confirmed that DKP is formed between the N-terminus and the amide of the nAsn residue side chain. A recent study by Brase and co-workers [79] also reported the formation of DKP when nAsn-type residues were introduced at a position adjacent to the N-terminal residue. The formation of DKP did not hinder the AIP thioester cyclization and produced a bicyclic AIP-III analog after purification.

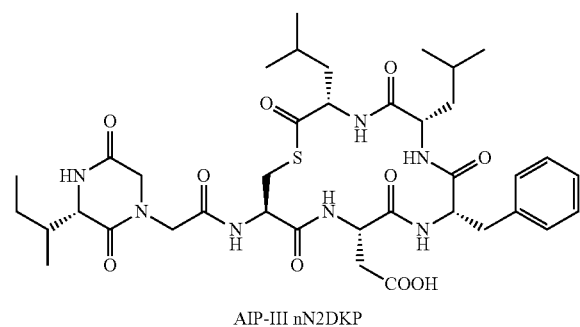 [SMILES: CCC(C)[C@@H]1NC(=O)CN(CC(=O)N[C@H]2CSC(=O)[C@H](CC(C)C)NC(=O)[C@H](CC(C)C)NC(=O)[C@H](Cc3ccccc3)NC(=O)[C@H](CC(=O)O)NC2=O)C1=O]

AIP-III nN2DKP

Furthermore, in the AIP-III nD4 analog, where the Asp4 residue was replaced with its peptoid residue counterpart (see FIG. 4), DKP formation was not observed despite common understanding that basic conditions enhance amine nucleophilicity and that ester bonds are more susceptible to cleavage than amide bonds.[74, 75, 76].

Example 3

Biological Reagents and Strain Information

All standard biological reagents were purchased from Sigma-Aldrich and used according to enclosed instructions. Suspended rabbit blood cells (10%, washed and pooled) were purchased from Lampire Biological Laboratories and stored at 4° C. until use in the hemolysis assay. Reagents for the TSST-1 enzyme-linked immunosorbent assay (ELISA) were purchased from Toxin Technology, Inc. Tryptic soy broth (TSB) and brain heart infusion (BHI) were prepared as instructed with pH=7.35.

The bacterial strains used in this study are listed in Table 2. Bacterial cultures were grown in a standard laboratory incubator at 37° C. with shaking (200 rpm) unless noted otherwise. The bacterial dilutions and incubation periods were chosen in each assay to provide the greatest dynamic range between positive and negative controls for each bacterial strain. Absorbance and fluorescence measurements were obtained using a Biotek Synergy 2 microplate reader using Gen5 data analysis software. All biological assays were performed in triplicate. $IC_{50}$ values were calculated using Graph Pad Prism software (v. 4.0) using a sigmoidal curve fit.

TABLE 2

S. aureus strains used in the biological assays listed according to group.

| Assay-type | Strain | Reference |
|---|---|---|
| Fluorescence | | |
| group-I | AH1677 | 58 |
| group-II | AH430 | 58, 59 |
| group-III | AH 1747 | 58 |
| group-IV | AH1972 | 58 |
| Hemolysis | | |
| group-I | RN6390B | 22 |
| group-II | RN6923 | 23 |
| group-III | MN8 | 60 |
| group-IV | RN4850 | 25 |
| β-Lactamase | | |
| group-I | RN9222 | 49 |
| group-II | RN9372 | 49 |
| group-III | RN9532 | 49 |
| group-IV | RN9371 | 49 |

Compound Handling Protocol.

Stock solutions of synthetic AIP compounds (1 mM) or cyclic dipeptides (10 mM) were prepared in DMSO and stored at 4° C. in sealed vials. The amount of DMSO used in biological screens did not exceed 2% (v/v). Polystyrene 96-well microtiter plates (Costar) were used for screening.

Example 4

Fluorescence-Based Reporter Gene Assays

The ability of compounds (e.g. of Table 1 or FIG. 4) to modulate the activity of the AgrC I-IV receptors was assessed using a fluorescence-based reporter gene assays (described below). Each compound was tested in group I-IV methicillin-resistant S. aureus (MRSA) strains harboring P3-gfp reporter plasmids.[58, 59] In these reporter plasmids, the agr P3 promoter, typically upstream of the main QS effector RNAIII, is positioned upstream of gfp. Thus, when bacterial cell densities and AIP concentrations are high, the AIP:AgrC complexes will phosphorylate AgrA, which will then bind P3 and transcribe gfp. GFP fluorescence can then be quantified to determine the extent of AgrC activation, and in these wild-type strains, will be observable in the absence of an exogenous AgrC modulator. Compounds capable of reducing fluorescence levels (or increasing these levels over background), therefore, can be classified as AgrC inhibitors (or activators).

In order to validate the reporter assay conditions and have controls for comparison to the new compounds, the activities of the native AIPs I-IV and the previously reported global inhibitor tAIP-I D2A [49] in also evaluated in each S. aureus reporter strain. The inhibitory trends for these peptides in each of the four AgrC receptors were comparable to previous reports using alternate *S. aureus* AgrC I-IV reporter strains. [49] Table 3 summarizes the activities of these control peptides and the compounds of the alanine and D-amino acid scans of AIP-III against AgrCs I-IV.

The reporter gene assay data revealed several interesting SAR trends for AIP-III, and a number of new, global AgrC inhibitors were uncovered with either comparable if not more potent activities than the known inhibitor tAIP-I D2A. There are two components to AIP:AgrC interactions: the initial recognition of an AIP by an AgrC receptor and the resultant induction of allosteric changes within AgrC that drives activation. To explore these components, two different SAR trends were examined: (i cross-inhibition of AgrC-I, -II, and -IV (namely AIP:AgrC recognition), and (ii) activation of AgrC-III (via allosteric changes).

D-amino acid and alanine replacement of either of the exocyclic tail residues (Ile1 or Asp2) of AIP-III resulted in compounds with similar cross-inhibitory activities to the parent AIP-III (Table 3, $IC_{50}$ values within error or <10-fold change). In addition, replacement of any one of the three hydrophobic, endocyclic residues in AIP-III (Phe5, Leu6, or Leu7) with alanine resulted in a significant loss of inhibition in groups-I, -II, and -IV (>10-fold change relative to AIP-III). Replacement of Phe5 and Leu6 with their D-amino acid counterparts displayed a >20-fold loss in inhibition in almost every case. However, AIP-III D-L7 displayed analogous inhibitory activities as the parent AIP-III in groups-I, -II and -IV (within error), suggesting that Leu7 may not enforce stereo defined interactions of AIP-III with AgrC receptors. This observation is congruent with previous findings for AIP-I by Williams and co-workers.[24] Two exceptions to these activity trends are noted. Replacing the endocyclic Phe5 or Leu6 with their D-isomers (in AIP-III D-F5 and AIP-III D-L6) neither maintained nor simply abolished inhibitory activity against one receptor, AgrC-II. These two analogs appeared to activate AgrC-II instead. The extent of this activation relative to native AIP could not be fully explored using the gfp-reporter assay, however, as the native AIP signals are produced at normal background levels in the *S. aureus* AgrC reporter strains (and thus an additive agonistic effect is measured).

The remaining two residues of AIP-III, Cys3 and Asp4, were found to contribute significantly to cross-receptor inhibition. The replacement of Cys3 with its D-isomer significantly reduced inhibition (>20-fold change relative to native AIP-III; Table 3). This reduction may be due to a conformational change caused by the reversed stereogenic center of cysteine, forcing a change in the orientation of the key hydrophobic residues in the macrocyclic backbone, thereby preventing AIP:AgrC recognition interactions.

Replacement of Asp4 with its D-isomer also reduced inhibition relative to AIP-III against AgrC-I by 28-fold, yet reduced inhibitory activity to a lesser degree against AgrC-II and AgrC-IV (4- and 3-fold relative to AIP-III, respectively). This result suggests that the stereochemistry of this residue could reinforce optimal orientations of Phe5 and Leu6 for interactions with AgrC-I.

The remaining two residues of AIP-III, Cys3 and Asp4, were found to contribute significantly to cross-receptor inhibition. The replacement of Cys3 with its D-isomer significantly reduced inhibition (>20-fold change relative to native AIP-III; Table 3). This reduction may be due to a conformational change caused by the reversed stereogenic center of cysteine, forcing a change in the orientation of the key hydrophobic residues in the macrocyclic backbone, thereby preventing AIP:AgrC recognition interactions. Replacement of Asp4 with its D-isomer also reduced inhibition relative to AIP-III against AgrC-I by 28-fold, yet reduced inhibitory activity to a lesser degree against AgrC-II and AgrC-IV (4- and 3-fold relative to AIP-III, respectively). This result suggests that the stereochemistry of this residue could reinforce optimal orientations of Phe5 and Leu6 for interactions with AgrC-I.

Perhaps more notable, however, was that the replacement of Asp4 with alanine (AIP-III D4A) increased the inhibitory activity of AIP-III by at least 10-fold in each group, delivering a picomolar global AgrC inhibitor. Interestingly, AIP-III D4A contains the identical mutation as the previously reported global inhibitor, tAIP-I D2A (residue numbering shifted (4→2) due to truncated structure), yet is a ~10-fold more active inhibitor in each group (Table 3). AIP-III D4A represented not only the most active inhibitor identified in this first series of AIP-III derivatives, but is also, to our knowledge, the most potent AgrC inhibitor to be reported.

TABLE 3

$IC_{50}$ values of the alanine, D-amino acid, N-methyl and peptoid scan derivatives of AIP-III against AgrC I-IV determined using *S. aureus* fluorescence reporter strains.[a]

| Compound name | Sequence | AgrC-I $IC_{50}$ (nM)[b] | AgrC-II $IC_{50}$ (nM)[b] | AgrC-III $IC_{50}$ (nM)[b] | AgrC-IV $IC_{50}$ (nM)[b] |
|---|---|---|---|---|---|
| AIP-III D-I1 | DI-N-(C-D-F-L-L) | 8.42 | 16.4 | 78.3 | 77.7 |
| AIP-III D-N2 | I-DN-(C-D-F-L-L) | 2.15 | 2.45 | 17.8 | 6.23 |
| AIP-III D-C3 | I-N-(DC-D-F-L-L) | >200 | >200 | >200 | >200 |
| AIP-III D-D4 | I-N-(C-DD-F-L-L) | 138 | 24.5 | >200 | 29.2 |
| AIP-III D-F5 | I-N-(C-D-DF-L-L) | >200 | >200 [c, e] | >200 | 174 |
| AIP-III D-L6 | I-N-(C-D-F-DL-L) | >200 | —[f] | >200 | >200 |
| AIP-III D-L7 | I-N-(C-D-F-L-DL) | 12.0 | 5.36 | —[f] | 10.5 |
| AIP-III I1A | A-N-(C-D-F-L-L) | 17.9 | 4.26 | 194 | 7.85 |
| AIP-III N2A | I-A-(C-D-F-L-L) | 3.60 | 0.732 | —[c, e] | 3.53 |
| AIP-III D4A | I-N-(C-A-F-L-L) | 0.485 | 0.429 | 0.0506 | 0.0349 |
| AIP-III F5A | I-N-(C-D-A-L-L) | >200 | >200 [c] | >200 | 118 |
| AIP-III L6A | I-N-(C-D-F-A-L) | >200 | >200 | >200 | >200 |
| AIP-III L7A | I-N-(C-D-F-L-A) | >200 | >200 | >200 | >200 |
| AIP-III N-Me-I1[b1] | NMeI-N-(C-D-F-L-L) | 60.8 | 12.8 | >1000 [c] | 49.2 |
| AIP-III N-Me-N2[b1] | I-NMeN-(C-D-F-L-L) | 8.04 | 3.19 | —[h] | 9.54 |
| AIP-III N-Me-C3[b1] | I-N-(NMeC-D-F-L-L) | 137 | 134 | —[h] | 106 |
| AIP-III N-Me-D4[b1] | I-N-(C-NMeD-F-L-L) | 172 | 7.98 | 90.2 | 36.9 |
| AIP-III N-Me-F5[b1] | I-N-(C-D-NMeF-L-L) | 4.49 | 1.95 | —[h] | 6.59 |
| AIP-III N-Me-L6[b1] | I-N-(C-D-F-NMeL-L) | >1000 [c] | —[h] | 162 | 81.6 |

TABLE 3-continued

IC$_{50}$ values of the alanine, D-amino acid, N-methyl and peptoid scan derivatives of AIP-III against AgrC I-IV determined using *S. aureus* fluorescence reporter strains.[a]

| Compound name | Sequence | AgrC-I IC$_{50}$ (nM)[b] | AgrC-II IC$_{50}$ (nM)[b] | AgrC-III IC$_{50}$ (nM)[b] | AgrC-IV IC$_{50}$ (nM)[b] |
|---|---|---|---|---|---|
| AIP-III N-Me-L7[b1] | I-N-(C-D-F-L-NMeL) | —[h] | —[h] | >1000[c] | —[h] |
| AIP-III nI1[b1] | nI-N-(C-D-F-L-L) | 44.0 | 4.25 | >1000[c] | 22.2 |
| AIP-III nN2 DKP[b1] | (I-nN)-(C-D-F-L-L) | 126 | 4.28 | 25.1 | 84.8 |
| AIP-III nD4[b1] | I-N-(C-nD-F-L-L) | 162 | 28.3 | 206 | 53.2 |
| AIP-III nF5[b1] | I-N-(C-D-nF-L-L) | 13.8 | 75.6 | >1000[c] | 0.839 |
| AIP-III nL6[b1] | I-N-(C-D-F-nL-L) | —[h] | —[h] | >1000[c] | >1000[c] |
| AIP-III nL7[b1] | I-N-(C-D-F-L-nL) | —[h] | —[h] | —[h] | —[h] |
| AIP-I[g] | Y-S-T-(C-D-F-I-M) | — | 8.00 | 0.522 | —[c,e] |
| AIP-II[g] | G-V-N-A-(C-S-S-L-F) | 1.62 | — | 0.532 | 0.396 |
| AIP-III[g] | I-N-(C-D-F-L-L) | 5.05 | 5.63 | — | 8.53 |
| AIP-IV[g] | Y-S-T-(C-Y-F-I-M) | —[c,d] | 0.373 | 0.460 | — |
| tAIP-I D2A[g] | Ac-(C-A-F-I-M) | 3.06 | 10.1 | 0.260 | 0.353 |

[a]See Examples for details of reporter strains and methods. All assays performed in triplicate.
[b]IC$_{50}$ values determined by testing AIPs over a range of concentrations (200 fM-10 μM) or
[b1](2.5 pM-10 μM).
[c] Dose response curve did not reach 100% inhibition over the concentrations tested.
[d] IC$_{50}$ values are between 100 nM-1 μM.
[e] Inhibition dose response curve upturned at higher concentrations.
[f]Dose response curve revealed agonism and no antagonism.
[g]Control compound.
[h]No inhibition was observed at the concentrations tested.

Analysis of the gfp screening data for the AIP-III analogs also provided valuable SAR trends for the activation of AgrC-III by AIP-III (Table 3). The exocyclic residue Ile1 of AIP-III appeared to play an important role in receptor activation. Replacing this residue with either alanine or the D-amino acid counterpart converted AIP-III to a weak antagonist (IC$_{50}$ values=194 nM and 78.3 nM, respectively). Converting the exocyclic residue Asn2 to its D-isomer yielded an even stronger AgrC-III antagonist (IC$_{50}$ value=17.8 nM). However, replacing Asn2 with alanine maintained agonistic activity, suggesting that the stereochemical presentation (and concomitant conformational constraints) of the peptide backbone may be more essential for AgrC-III activation relative to the composition of the Asn2 side chain. Within the AIP-III macrocycle, the two hydrophobic residues Phe5 and Leu6 proved to be crucial for AgrC-III activation, as D-isomer or Ala replacements at either of these residues gave relatively inactive analogs that only weakly inhibited AgrC-III activity (IC$_{50}$ values>200 nM). In contrast, AIP-III D-L7 maintained the agonistic activity of the parent AIP-III, while AIP-III L7A was largely inactive, similar to the AIP-III F5A and AIP-III L6A mutants. This disparate activity trend suggests that Leu7 may not play as a major of a role in AIP-III:AgrC-III interactions as Phe5 and Leu6.

Replacement of the AIP-III Cys3 with its D-isomer gave a weakly active inhibitor (IC$_{50}$ value >200 nM; Table 3), indicating that the stereochemistry of this residue is important to AIP-III:AgrCIII interactions. Similarly, substitution of Asp4 with D-Asp also yielded an inactive analog (IC$_{50}$ value >200 nM). As discussed above, however, replacing this same residue with alanine (AIP-III D4A) produced the most potent AgrC-III inhibitor in this series (IC$_{50}$ value=0.0506 nM).

Together, these SAR trends indicate that Asp4, adjacent to the conserved Cys3 residue, plays a major role in AgrC activation, but not in recognition by the receptor. Throughout these SAR analyses, it was assumed that the AIP-III analogs were eliciting their activity through directly binding AgrC receptors and outcompeting the native AIP signals. This is a reasonable assumption in view of the structural relationship of these mutants to the native AIP signals, and has been made in prior studies of AIP-I and -II analogs. However, to provide further support for this hypothesis, we performed a competition assay between the native AIPs and our most potent AgrC-III inhibitor, AIP-III D4A, using the gfp reporter strains. The native AIP signals could be added in a dose-dependent manner to completely eliminate AIP-III D4A inhibition and recover gfp production in each of the four *S. aureus* groups (see FIGS. 2A-D). These data serve to support a competitive mechanism by which AIP-III D4A and the related analogs in this study modulate AgrC activity.

Table 3 also summarizes the activities of these control peptides and the peptidomimetics of FIG. 4. As noted above, exocyclic residues of AIPs are required for cognate activation but not receptor recognition. Consistent with previous observations, peptidomimetics with modifications to the exocyclic tail residues had activities similar to the parent AIP-III. AIP-III nN2 could not be directly evaluated, but note that the bicyclic AIP-III nN2 DKP significantly lost ability to inhibit AgrC-I (>20-fold change).

With respect to changes in the macrocycle, the importance of the conserved cysteine and three hydrophobic residues was confirmed as most of such modifications resulted in significant reduction of potency (>9-fold change). Furthermore, modifications of Leu6 resulted in AgrC-II agonists, an observation similar to that observed on its replacement with the D-amino acid. While, Phe5 could not be mutated to a D-amino acid or alanine without loss of activity, Phe5 could be mutated with peptidomimetics. For example, the replacement of Phe5 with the N-methyl analog had no effect on inhibition relative to AIP-III (IC$_{50}$ values within error) and the insertion of a peptoid residue resulted in a picomolar group-IV inhibitor. AIP-III nF5 was the most potent inhibitor identified for any group in these studies and displayed enhanced potency for AgrC-IV only (versus AIP-III: 10-fold increased potency for AgrC-IV, within error for AgrC-I, and 13-fold reduction for AgrC-II). In contrast replacement of Leu7 with the N-methylated or peptoid analog abolished inhibition where peptoid insertion resulted in an AgrC-II agonist. The combined results indicate that the side chain of Phe5 (but not the backbone) is the important component of this residue, and the backbone is the important component of Leu7. Based on these results, the AIP segment spanning from the Phe5 α-carbon to the nitrogen atom of Leu7 appears to be the basis for AgrC recognition.

The SAR analysis also provided information related to AgrC-III activation by AIP-III. Agonism of AgrC-III was not detected for any of the backbone-modified analogs, indicating that hydrogen bonding throughout the entire sequence is important for activation. However, the utilization of wild-type bacteria in our assay prevents accurate assessment of this phenomenon. Furthermore, of the 13 peptidomimetic analogs of FIG. 4, only AIP-III nN2 DKP was found to be an AgrC-III inhibitor. This analog also significantly reduced TSST-1 production by a group-III *S. aureus* strain in low μM concentrations.

Examination of the peptidomimetics of FIG. 4 identified group-selective inhibitors. Two selective inhibitors were identified after replacement of Asp4 with either the N-methyl amino acid or the corresponding peptoid: AIP-III N-Me D4 and AIP-III nD4, respectively. These compounds were both selective AgrC-II and -IV inhibitors ($IC_{50}$ values for AgrC-I and -III were greater than 100 nM). This result is consistent with observation regarding the replacement of Asp4 with its D-stereoisomer, which only exhibited weak inhibition activity against AgrC-I, but maintained antagonism activity against AgrC-II and -IV in the gfp reporter assay. The intolerance of AgrC-I to changes at Asp4 may be attributable to the sequence of the cognate AIP that has an Asp residue at the same position. Additionally an AgrC-IV selective inhibitor, AIP-III N-Me-L6, was identified on N-methylation of Leu6 of AIP-III. The selectivity obtained through this subtle change in the AIP structure emphasizes the specificity of the interactions between the AIPs and the AgrC receptors. Further, two partially selective inhibitors, AIP-III nF5 and AIP-III nN2 DKP ($IC_{50}$ values vary significantly between the groups) were identified. Group-selective inhibitors, for example, are useful as research reagents to study the agr QS circuit of *S. aureus* in mixed bacterial milieu. Group-selective inhibitors provide a method to temporally evaluate mixed strains to probe not only strain-strain competition, but also to assess the role of QS timing on a strain's success or failure in such competition.

Compounds of Table 1 with double and triple alanine changes, alternate aromatic residues in place of Phe5, and truncated and elongated exocyclic tails were evaluated in the four *S. aureus* gfp-reporter strains for inhibitory activity against AgrC-I-IV. The results of these assays are shown in Table 4; data for AIP-III D4A, and the previously reported inhibitor, tAIP-I D2A, are included for comparison.

TABLE 4

$IC_{50}$ values of the second-generation AIP-III analogues against AgrC I-IV determined using *S. aureus* fluorescence reporter strains.[a]

| Compound name | Sequence | AgrC-I $IC_{50}$ (nM)[b] | AgrC-II $IC_{50}$ (nM)[b] | AgrC-III $IC_{50}$ (nM)[b] | AgrC-IV $IC_{50}$ (nM)[b] |
|---|---|---|---|---|---|
| AIP-III I1A/N2A | A-A-(C-D-F-L-L) | 7.40 | 4.38 | 2.60 | 5.41 |
| AIP-III I1A/D4A | A-N-(C-A-F-L-L) | 0.328 | 2.35 | 0.280 | 0.101 |
| AIP-III N2A/D4A | I-A-(C-A-F-L-L) | 0.331 | 0.204 | 0.0657 | 0.0221 |
| AIP-III I1A/N2A/D4A | A-A-(C-A-F-L-L) | 0.304 | 0.604 | 0.0734 | 0.0161 |
| tAIP-III | Ac-(C-D-F-L-L) | 26.7 | 1.53 | >200 | 25.5 |
| tAIP-III D2A | Ac-(C-A-F-L-L) | 0.257 | 0.900 | 0.329 | 0.0957 |
| tAIP-III D2A/F3Y | Ac-(C-A-Y-L-L) | 0.279 | 1.15 | 0.387 | 0.0306 |
| tAIP-III D2A/F3W | Ac-(C-A-W-L-L) | 0.909 | 1.90 | 0.509 | 0.0363 |
| Ac-AIP-III | Ac-I-N-(C-D-F-L-L) | >200 | 44.3 | >200 | >200 |
| G-AIP-III | G-I-N-(C-D-F-L-L) | 29.9 | 13.7 | >200[c] | 104 |
| A-AIP-III | A-I-N-(C-D-F-L-L) | 26.1 | 6.40 | 27.5[d] | 28.5[d] |
| Y-AIP-III | Y-I-N-(C-D-F-L-L) | 8.92 | 3.75 | 39.2 | 78.2[c] |
| AIP-III D4A[e] | I-N-(C-A-F-L-L) | 0.485 | 0.429 | 0.0506 | 0.0349 |
| tAIP-I D2A[e] | Ac-(C-A-F-I-M) | 3.06 | 10.1 | 0.260 | 0.353 |

[a] See Experimental Section for details of reporter strains and methods. All assays performed in triplicate.
[b] $IC_{50}$ values determined by testing AIPs over a range of concentrations (200 fM-10 μM).
[c] Dose response curve did not reach 100% inhibition over the concentrations tested.
[d] Antagonism dose response curve upturned at higher concentrations.
[e] Data included for comparison.

The analogs with double and triple alanine mutations (Table 4, Rows 1-4) were designed to examine whether simultaneously replacing multiple amino acid residues with alanine would result in an additive effect on compound activity. Replacing both exocyclic residues (Ile1 and Asn2) in AIP-III with alanine yielded an analog (AIP-III I1A/N2A) with an $IC_{50}$ value between those of the parent single alanine mutants for AgrC-I, -II, and -IV (see Tables 3 and 4). In contrast, AIP-III I1A/N2A was a much more potent inhibitor against AgrC-III ($IC_{50}$=2.60 nM) relative to the single alanine mutants (I1A, $IC_{50}$=194 nM; N2A=weak agonist). Introducing a D4A mutation along with these exocyclic alanine mutations (Table 4, Rows 2-4) yielded analogs with antagonistic activities analogous to the AIP-III D4A parent mutant, regardless of other mutations (within error for all except AIP-III I1A/D4A against AgrC-II, with a <5-fold change), indicating that the inclusion of D4A may convert every AIP-III mutant to cross-group AgrC inhibitor.

Four truncated AIP-III derivatives lacking exocyclic tails were prepared to explore whether this modification, as shown for AIP-I, -II and -IV,[49] could broaden their inhibitory scope against cognate and non-cognate AgrC receptors (Table 4, Rows 5-8). Such an analysis of the native AIP-III is yet to be reported. It was found that the truncated AIP-III (tAIP-III) was largely inactive in its cognate receptor, AgrC-III. Moreover, no significant activity change between tAIP-III and native AIP-III against AgrC-II and -IV was observed, and slightly diminished activity for tAIP-III relative to native AIP-III against AgrC-I (26.7 nM v. 5.05 nM, respectively) was observed. These data suggest that the exocyclic tail of AIP-III does not play a major role in cross-group inhibition. The inclusion of the D4A mutation in the truncated AIP-III produced a potent global AgrC inhibitor (termed tAIP-III D2A; <1 nM for all groups; note, residue numbering shifted due to truncation), with activity within error of its full-length analog (AIP-II D4A) in AgrC-I, -II, and -IV and only somewhat reduced for group-III (0.329 nM v. 0.0506 nM, respectively). This truncated AIP-III analog represents a more structurally streamlined, peptide-based AgrC inhibitor.

To explore SARs for the potent inhibitor tAIP-III D2A, Phe3 was replaced with other aromatic amino acids (Tyr or Trp) to determine the role of this residue in inhibitory activity. These two analogs (tAIP-III D2A/F3Y and tAIP-III D2A/F3W) displayed similar inhibitory activities in the gfp-reporter assays as the parent analog. These data, along with the alanine scan data above, suggest that bulky, aromatic residues are important at the Phe3 (or Phe5) position for AgrC inhibition by AIP-III analogs, but that the residue identity is not critical.

Four elongated AIP-III analogs with either an acetyl, glycine, alanine, or tyrosine extension at the N-terminus of AIP-III. The tyrosine-extended AIP-III (Y-AIP-III) was a moderate antagonist of AgrC-III in the gfp-reporter assay. In contrast, the acetylated and glycine variants (Ac-AIP-III and G-AIP-III) were largely inactive in AgrC-III, and the alanine-extended AIP (A-AIP-III) was actually a partial agonist of AgrC-III instead. When evaluated for modulatory activity in the non-cognate AgrC receptors, Ac-AIP-III was the least active (>200 nM for group-I and -IV and 44.3 nM for group-II), implying that a free N-terminus is important for recognition. None of the amino acid AIP-III analogs showed improved inhibition compared to the parent AIP-III, and G-AIP-III was the least potent extended amino acid analog overall. Interestingly, the A-AIP-III, but not Y-AIP-III-(Tyr being first amino acid in the native AIP-IV octapeptide sequence), actually displayed partial agonism in AgrC-IV.

Representative Assay Protocol.

Peptide stock solutions were diluted with DMSO in serial dilutions (either 1:3, 1:5, or 1:10), and 2 µL of the diluted solution was added to each of the wells in a black 96-well microtiter plate. An overnight culture of S. aureus gfp strain was diluted 1:50 with fresh TSB (pH 7.35). A 198-µL portion of diluted culture was added to each well of the microtiter plate containing peptide. Plates were incubated at 37° C. for 24 h. Fluorescence (EX 500 nm/EM 540 nm) and $OD_{600}$ of each well was then recorded using a plate reader and $IC_{60}$ values were calculated. For the competition assays, 2 µL of AIP-III D4A stock solution was added to wells in a black 96-well microtiter plate to final concentrations of 2 nM (group-I and -II strains) or 0.3 nM (group-III and -IV strains). Native AIP (I-IV) stock solutions were diluted with DMSO in serial dilutions (1:3 dilutions) and added to the wells containing AIP-III D4A. The fluorescence assay was carried out as described above in the four respective S. aureus reporter strains.

Example 5

Hemolysis Assays

The response of S. aureus gfp-reporters may not accurately reflect physiologically relevant QS phenotypes. Previous studies have established that the production of hemolysins is regulated by the agr QS system.[18-20] Therefore, analogs that inhibit the agr system should also block the production of hemolysins in S. aureus. Inhibition of the agr system should then be readily quantitated by hemolysis assays using red blood cells. To this end, a standard bacterial hemolysis assay was modified to a 96-well microtiter plate format to expedite compound screening [65, 66] All 13 compounds evaluated in Table 3 were further evaluated for their ability to inhibit hemolysis by S. aureus. Wild-type strains of S. aureus groups-I-IV were treated with compounds to be tested and the cultures were then assessed for hemolysin activity. Rabbit red blood cells were incubated with peptide-treated bacterial cultures (~15 min) in a microtiter plate, after which the samples were pelleted by centrifugation. The culture supernatant was then transferred to new plates, and the concentration of free heme (directly correlated with red blood cell lysis) was quantified by measuring absorbance at 420 nm. Similar to the gfp-reporter assays outlined above, the native AIPs (I-IV) and the previously reported global inhibitor tAIP-I D2A as controls in the hemolysis assays. Table 5 summarizes the hemolysis assay data.

With a few minor exceptions, the relative $IC_{50}$ value trends for the controls and AIP analogs in the hemolysis assay were largely identical to those in the gfp-reporter assays. Note that the two sets of assay data came from different bacterial strains, and thus strain-to-strain variations could account for the slight deviations observed. The most potent AgrC inhibitors identified in the gfp-reporter assays were capable of completely inhibiting hemolysis in the S. aureus strains at nanomolar concentrations or lower. For example, the global S. aureus QS inhibitor identified in the gfp-reporter assay, AIP-III D4A, inhibited hemolysis in all four groups at sub-nanomolar concentrations ($IC_{50}$ value <0.2 nM). This peptide was three-fold more active than the previously reported global inhibitor, tAIP-I D2A, in the hemolysis assay in the group IV strain; more strikingly, it was 40-fold more active in the group-II strain. These data are significant, as they indicate that AIP-III D4A and other compounds of this invention are capable of blocking an important QS phenotype directly linked to virulence in wild-type S. aureus strains.

TABLE 5

$IC_{50}$ values of the alanine and D-amino acid scan analogs of AIP-III against AgrC I-IV determined using the hemolysis assay.[a]

| Compound | Sequence | AgrC-I $IC_{50}$ (nM)[b] | AgrC-II $IC_{50}$ (nM)[b] | AgrC-III $IC_{50}$ (nM)[b] | AgrC-IV $IC_{50}$ (nM)[b] |
|---|---|---|---|---|---|
| AIP-III D-I1 | DI-N-(C-D-F-L-L) | 18.4 | 2.67 | >200[c] | >200 |
| AIP-III D-N2 | I-DN-(C-D-F-L-L) | 5.31 | 0.222 | —[c,d] | 23.1 |
| AIP-III D-C3 | I-N-(DC-D-F-L-L) | >200 | 122 | >200 | >200 |
| AIP-III D-D4 | I-N-(C-DD-F-L-L) | 77.0 | 1.15 | >200 | >200[d] |
| AIP-III D-F5 | I-N-(C-D-DF-L-L) | >200 | >200 | >200 | >200 |
| AIP-III D-L6 | I-N-(C-D-F-DL-L) | >200 | >200 | >200 | >200 |
| AIP-III D-L7 | I-N-(C-D-F-L-DL) | 29.3 | 1.96 | —[e] | 47.8 |
| AIP-III I1A | A-N-(C-D-F-L-L) | 4.61 | 1.29 | —[f] | 12.5 |

TABLE 5-continued

IC$_{50}$ values of the alanine and D-amino acid scan analogs of AIP-III against AgrC I-IV determined using the hemolysis assay.[a]

| Compound | Sequence | AgrC-I IC$_{50}$ (nM)[b] | AgrC-II IC$_{50}$ (nM)[b] | AgrC-III IC$_{50}$ (nM)[b] | AgrC-IV IC$_{50}$ (nM)[b] |
|---|---|---|---|---|---|
| AIP-III N2A | I-A-(C-D-F-L-L) | 1.02 | 0.137 | —[c,d] | 2.64 |
| AIP-III D4A | I-N-(C-A-F-L-L) | 0.0820 | 0.0596 | 0.163 | 0.106 |
| AIP-III F5A | I-N-(C-D-A-L-L) | >200 | 44.7 | >200 | >200 |
| AIP-III L6A | I-N-(C-D-F-A-L) | >200 | >200 | >200 | >200 |
| AIP-III L7A | I-N-(C-D-F-L-A) | >200 | >200 | >200 | >200 |
| AIP-I[g] | Y-S-T-(C-D-F-I-M) | — | 3.34 | 6.12 | 189 |
| AIP-II[g] | G-V-N-A-(C-S-S-L-F) | 0.890 | — | 3.59 | 1.19 |
| AIP-III[g] | I-N-(C-D-F-L-L) | 8.07 | 0.456 | — | 23.8 |
| AIP-IV[g] | Y-S-T-(C-Y-F-I-M) | —[c,d] | 0.0897 | 1.49 | — |
| tAIP-I D2A[g] | Ac-(C-A-F-I-M) | 1.45 | 2.50 | 0.853 | 0.361 |

[a]See Experimental Section for details of reporter strains and methods. All assays performed in triplicate.
[b]IC$_{50}$ values determined by testing AIPs over a range of concentrations (200 fM-10 μM).
[c]Dose response curve did not reach 100% inhibition over the concentrations tested.
[d]Dose response curve upturned at higher concentrations.
[e]Dose response curve revealed agonism and no inhibition.
[f]No activity at any concentration tested up to at least 10 μM.
[g]Control compound.

The most potent AgrC inhibitors from Table 4 (IC$_{50}$ values less than 1 nM) were also evaluated in the *S. aureus* hemolysis assay (Table 6). The trends for these compounds analogs in the hemolysis and gfp-reporter assays are largely consistent. The hemolysis assay did unmask variances between certain potent compounds. For example, AIP-III I1A/D4A inhibited hemolysis in group-I at eightfold lower concentrations than the original AIP-III D4A analog (0.0103 nM v. 0.0820 nM, respectively), a discrepancy that was not observed in the gfp reporter assays (0.328 nM v. 0.485 nM), suggesting that double mutants may enhance the inhibitory activity of AIP-III analogs. AIP-III D-D4 was a strong AgrC-IV antagonist in the gfp assay (IC$_{50}$ value=29.2 nM), but displayed partial agonism in the hemolysis assay (IC$_{50}$ value >200 nM).

TABLE 6

IC$_{50}$ values of selected second-generation AIP-III analogues against AgrC I-IV determined using the hemolysis assay.[a]

| Compound | Sequence | AgrC-I IC$_{50}$ (nM)[b] | AgrC-II IC$_{50}$ (nM)[b] | AgrC-III IC$_{50}$ (nM)[b] | AgrC-IV IC$_{50}$ (nM)[b] |
|---|---|---|---|---|---|
| AIP-III I1A/D4A | A-N-(C-A-F-L-L) | 0.0103 | 0.793 | 0.551 | 0.284 |
| AIP-III N2A/D4A | I-A-(C-A-F-L-L) | 0.0362 | 0.0661 | 0.216 | 0.122 |
| AIP-III I1A/N2A/D4A | A-A-(C-A-F-L-L) | 0.0411 | 0.0606 | 0.243 | 0.140 |
| tAIP-III D2A | Ac-(C-A-F-L-L) | 0.332 | 0.711 | 0.197 | 0.306 |
| tAIP-III D2A/F3Y | Ac-(C-A-Y-L-L) | 0.279 | 0.204 | 0.265 | 0.134 |
| tAIP-III D2A/F3W | Ac-(C-A-W-L-L) | 0.468 | 0.126 | 1.08 | 0.194 |

[a]See Experimental Section for details of reporter strains and methods. All assays performed in triplicate.
[b]IC$_{50}$ values determined by testing AIPs over a range of concentrations (200 fM-10 μM).

TABLE 7

Conditions for hemolysis assay

| *S. aureus* strain | Dilution of culture with TSB | Bacteria + AIPs Incubation time (h) | Culture + red blood cells incubation time (min) |
|---|---|---|---|
| RN6390B (group-I) | 1:100 | 8 | 15 |
| RN9623 (group-II) | 1:25 | 8 | 15 |
| MN8 (group-III) | 1:10 | 6 | 25 |
| RN4850 (group-IV) | 1:10 | 6 | 15 |

TSB = tryptic soy broth.

Representative Assay Protocol.

Peptide stock solutions were diluted with DMSO in serial dilutions (either 1:3, 1:5, or 1:10 dilutions). For hemolysis assays, 2 μL of diluted peptide solution was added to each of the wells in a 96-well microtiter plate. An overnight culture of *S. aureus* wild-type strain was diluted with fresh TSB (pH 7.35) (1:10, 1:25 or 1:100, assay conditions dependent on strain (see Table 7). A 198-μL portion of the diluted culture was added to each well of the microtiter plate containing peptides.

Plates were incubated statically at 37° C. for 6-8 h. The cultures were then assayed for hemolytic activity. Suspended rabbit red blood cells (1 mL) were centrifuged (2,000 rpm, 2 min, 25° C., 450 g), the supernatant was removed, and the cells were resuspended in saline phosphate buffer (PBS, pH=7.35, 1 mL). After the OD$_{600}$ of each well of the 96-well microtiter plate was recorded, a 13-μL portion of the suspended red blood cells was added to each well. After 15-25 min (see Table 7) of static incubation at 37° C., the microtiter plates were centrifuged to pellet the cells (4 min, 25° C., 450 g). A 150-μL portion of supernatant from each well of culture was transferred to a fresh 96-well microtiter plate. Absorbance at 420 nm was measured for each well using a plate reader and $IC_{60}$ values were calculated.

Example 6

Attenuation of TSST-1 Production

Figure 3:
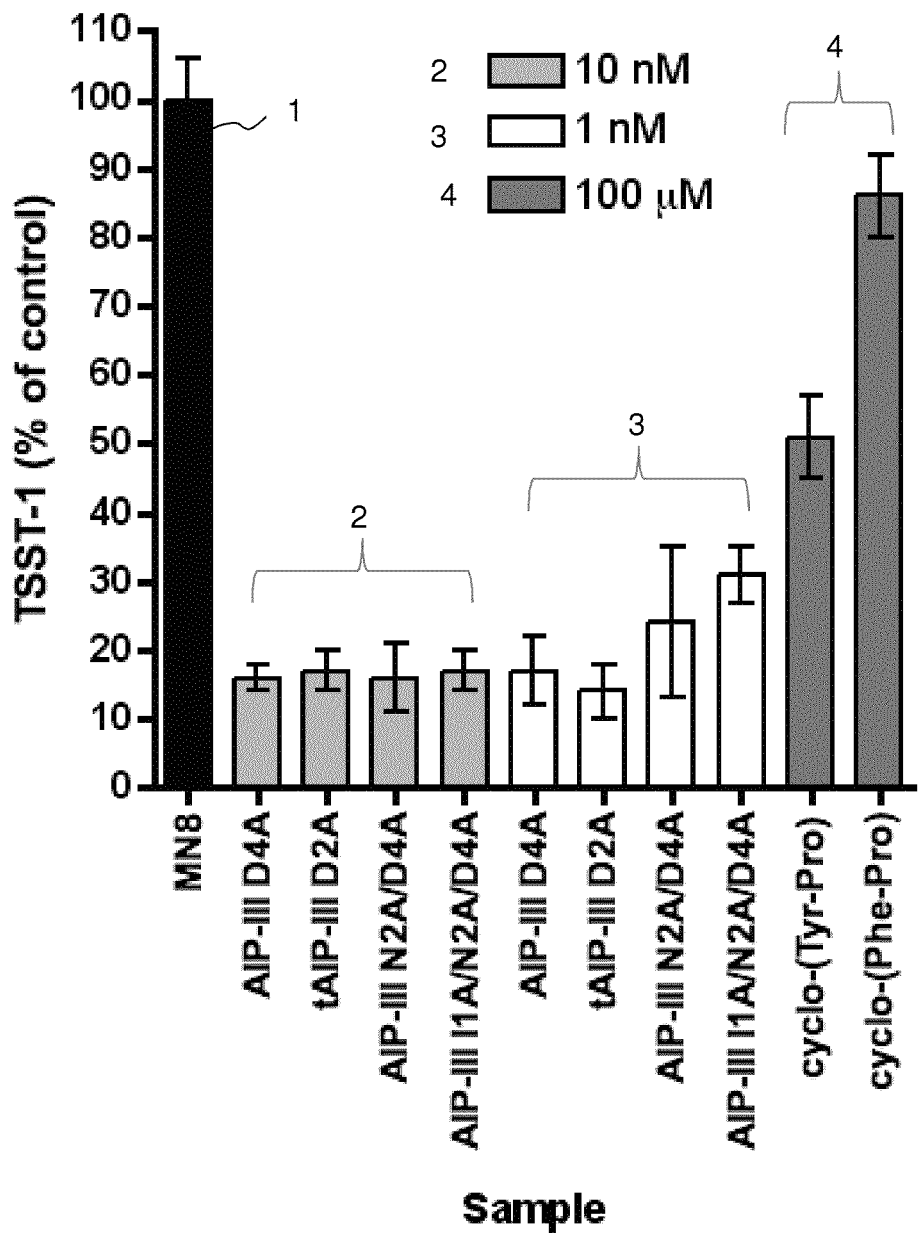
FIG. 3 is a graph illustrating attenuation of TSST-1 production in wild-type group-III *S. aureus* (MN8) using selected compounds of the invention. Bacteria were either untreated (black bar, 1), treated with AIP analogs at 10 nM (light gray bars, 2) or 1 nM (white bars, 3), or treated with previously reported cyclic dipeptides at 100 μM (dark gray bars, 4). TSST-1 concentrations are presented as percentage of the TSST-1 concentration in untreated cultures.

The production of TSST-1 is a hallmark QS phenotype *S. aureus* group-III. The four most potent AgrC inhibitors identified above (AIP-III D4A, tAIP-III D2A, AIP-III N2A/D4A, and AIPIIII1A/N2A/D4A) were evaluated for the capability of reducing the production of TSST-1 in group-III *S. aureus*. A wild-type group-III *S. aureus* strain (MN8) known to produce TSST-1 in the presence of each AIP-III analog (at 1 and 10 nM), and quantitated toxin production using a standard sandwich-type ELISA assay with a commercially available anti-TSST-1 antibody. The results of these assays are shown in FIG. 3, and show that all four AIP-III analogs are capable of strongly inhibiting TSST production (by >80%) in this group-III *S. aureus* strain at 10 nM. Moreover, two analogs, AIP-III D4A and tAIP-III D2A, maintained 80% reduction of TSST-1 levels at 1 nM.

These ELISA data are significant, as they demonstrate that compounds of this invention are capable of inhibiting TSST-1 production in *S. aureus*. Previously, bacterial supernatants containing the naturally occurring cyclic dipeptides (cyclo-(Tyr-Pro) and cyclo-(Phe-Pro)) were reported by McCormick and co-workers.[29] to reduce TSST-1 production levels by ~80% using an analogous ELISA assay. The purified cyclic dipeptides, however, were not tested in the ELISA. To perform a more quantitative comparison of the most potent AIP-III analogs to these cyclic peptides, pure samples of cyclo-(Tyr-Pro) or cyclo-(PhePro) were subjected to the ELISA protocol, and it was found that 100 μM concentrations were required to reduce TSST production by ~50% or 80%, respectively (see FIG. 3). These data indicate that the compounds of this invention tested are at least 1000-fold more potent than the cyclic dipeptides in the ELISA, and thus represent some of the most potent inhibitors of TSST-1 production in *S. aureus* to be reported.

TSST-1 ELISA Assay Protocol

The TSST-1 ELISA protocol was based in part on the procedure supplied by the toxin producer (Toxin Technologies, Inc.), with some modifications. Peptide stock solutions (AIP-III analog or cyclic dipeptide control) were diluted with DMSO to the desired concentration, and 20 μL of the diluted solutions was added to 15-mL Falcon tubes. An overnight culture of *S. aureus* MN8 was diluted 1:100 with fresh BHI (pH 7.35), and a 1-mL portion of diluted culture was added to each Falcon tube containing peptide. The cultures were incubated at 37 C for 24 h. Simultaneously, rabbit polyclonal anti-TSST-1 IgG (100 μL, 10 μg/mL in coating buffer (0.01 M sodium carbonate, pH 9.6)) was added to a 96-well ELISA plate and incubated with shaking (200 rpm) in a humid chamber at 37° C. for 18 h. The ELISA plate was then washed 3× (300 μL each, PBS solution containing 0.05% Tween-20, PBS-Tween). To block the plate, bovine serum albumin (BSA, 1% in PBS-Tween, 100 μL) was added to each well and incubated for 15 min at rt, after which it was washed 3× again with PBS-Tween (300 μL each). The bacterial cultures were centrifuged to pellet the cells (10 min, 25° C., 450 g), and the supernatants were sterile filtered. The supernatants were diluted 1:10 in normal rabbit serum (NRS, 1% in PBS-Tween) and incubated for 15 min at rt. The incubated solutions were further diluted using PBS-Tween to a total dilution of 1:100 to 1:2,000. The diluted supernatant samples (100 μL) and TSST-1 standards with known concentrations (ranging from 10 ng/mL to 0.32 ng/mL, 100 μL) were added to the ELISA plate and incubated with shaking (200 rpm) in a humid chamber at 37° C. for 2 h. After incubation, the plate was washed 3× with PBS-Tween, and anti-TSST-1 IgG horseradish peroxidase conjugate (100 μL, 3.33 μg/mL) was added and incubated with shaking (200 rpm) in a humid chamber at 37° C. for 1 h. The plate was washed 5× with PBS-Tween, after which 2,2'-azinobis(3-ethylbenzthiazoline-sulfonic acid) (ABTS solution, 100 μL) was added and incubated at rt for 15 min. Absorbance at 405 nm was measured using a plate reader, and a TSST-1 standard curve was constructed for each assay plate using the data of the TSST-1 reference standards. (The R2 of linear regression analysis for these data was ≥0.99.) The TSST-1 concentration in the test samples were then determined from the regression equation and presented as a percentage of the TSST-1 concentration in the untreated cultures.

Example 7

Activation Assay-β-Lactamase Assay

Peptidomimetic compounds of FIG. 4 that displayed <100% inhibition of gfp production in the wild-type strains were assessed for agonistic activity using a set of *S. aureus* group-I agr-null strains each carrying a plasmid containing a P3-blaZ fusion (to confer β-lactamase activity in response to AgrC activation) and agrCA from groups-I, -II, -III, or -IV. [46, 49]. None of peptidomimetics of FIG. 4 were able to activate the non-cognate AgrC receptors in the activation assay. Only the ability of the N-methyl and peptoid scans of AIP-III to activate the AgrC-III receptor is presented in Table 8.

Four of the compounds tested were found to activate AgrC-III. N-methylation of Asn2 produced an analog with enhanced activity compared to AIP-III (Table 8), combined with the relatively high antagonistic activity of AIP-III nN2 DKP, this result suggests that N-alkylation of Asn2 is beneficial for AgrC-III interactions. N-methylation of Cys3 resulted in an analog with reduced activity compared to AIP-III (>10-fold change, Table 5), further highlighting the importance of this residue for effective AgrC receptor recognition. Modifying Phe5 did not hamper the ability of the resulting analogs to activate AgrC-III (Table 8). This result is consistent with the hypothesis that the AIP segment spanning from the Phe5 α-carbon to the nitrogen atom of Leu7 is the basis for AgrC recognition.

TABLE 8

$EC_{50}$ values for the N-methyl and peptoid scan analogs of AIP-III against AgrC-III determined using a β-lactamase reporter strain.[a]

| Peptide name | Sequence | AgrC-III $EC_{50}$ (nM)[b] |
|---|---|---|
| AIP-III | I-N-(C-D-F-L-L) | 102 |
| AIP-III N-Me-N2 | I-NMeN-(C-D-F-L-L) | 19.0 |
| AIP-III N-Me-C3 | I-N-(NMeC-D-F-L-L) | >1000 |
| AIP-III N-Me-F5 | I-N-(C-D-NMeF-L-L) | 49.6 |
| AIP-III nF5 | I-N-(C-D-nF-L-L) | 202 |

[a]Example 7 for details of reporter strains, and experimental procedures. All assays performed in triplicate.
[b]$EC_{50}$ values determined by testing AIPs over a range of concentrations (2.5 pM-10 μM).

β-Lactamase Assay Protocol

Peptide stock solutions were diluted with DMSO in serial dilutions (1:5), and 2 μL of the diluted solution was added to each of the wells in a clear 96-well microtiter plate. An overnight culture of S. aureus β-Lactamase strain was diluted 1:50 with fresh BHI (pH 7.35) and the bacteria was incubated in a shaker until it reaches early exponential phase ($OD_{600}$=0.16). A 50-μL portion of culture was added to each well of the microtiter plate containing peptide. Plates were incubated at 37° C. for 1 h. $OD_{600}$ of each well was recorded using a plate reader, followed by the addition of sodium azide (5 μL of 50 mM solution) and Nitrocefin solution (50 μL of 132 μg/mL in 0.1 M sodium phosphate buffer, pH 5.8). The plate was shaken in an incubator at 37° C. in the dark for 20 min, the absorbance (495 nm) of each well was then recorded and $EC_{50}$ values were calculated.

Example 8

Figure 5:
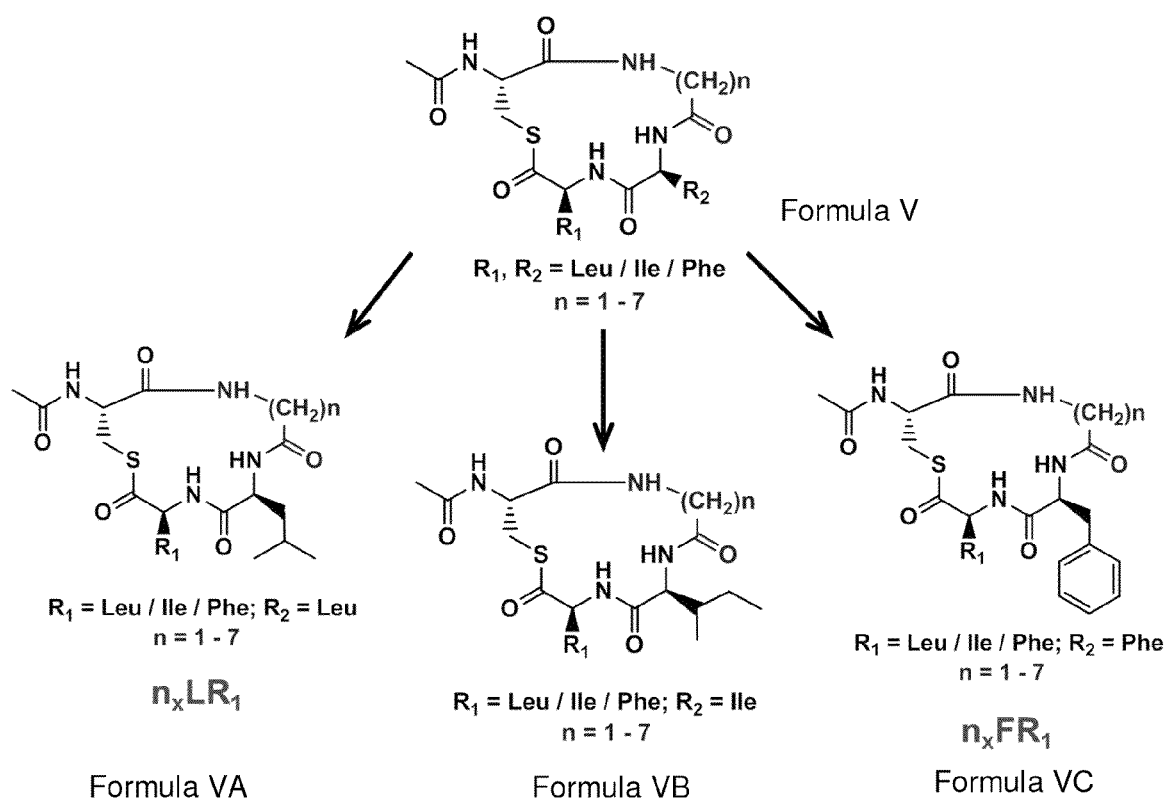
FIG. 5 illustrates exemplary compounds of this invention of formula V.

Synthesis of Compounds of Formula V and Biological Assessment of Inhibition of AgrC Receptor Groups Synthetic methods described above were employed to prepare compounds of Formula V, and VA-C which are illustrated in FIG. 5. Scheme 3 illustrates the application of these methods to the synthesis of these compounds.

FIG. 5 illustrates the naming scheme for certain compounds of Formula V which is used in Table 9. Table 9 provides a comparison of activity of certain compounds of formula V for inhibition of AgrC Receptor Groups of S. aureus. Table 9 lists % activation for each listed compound for AgrC groups I-IV. Percent activation is a comparison of fluorescence measurements (performed essentially as described in Example 4) of treated bacteria to non-treated wild-type bacteria (S. Aureus) which produce native-ligand which activates QS in the absence of an inhibitor; a lower % activation indicates more potent inhibition. This study identifies several compounds which potently inhibit AgrC receptors at the nM level. Specifically compound designated n3LF is a global inhibitor of all four AgrC receptors. Specifically, the compound designated n2LF is a selective group-II inhibitor. Specifically, the compounds d designated n5LF and n7LF are selective group-III inhibitors. Structures of certain compounds of formula V are listed below indicating $IC_{50}$ values for inhibition of listed AgrC receptors:

Scheme 3: Synthetic method of synthesis of exemplary compounds of Formula V.

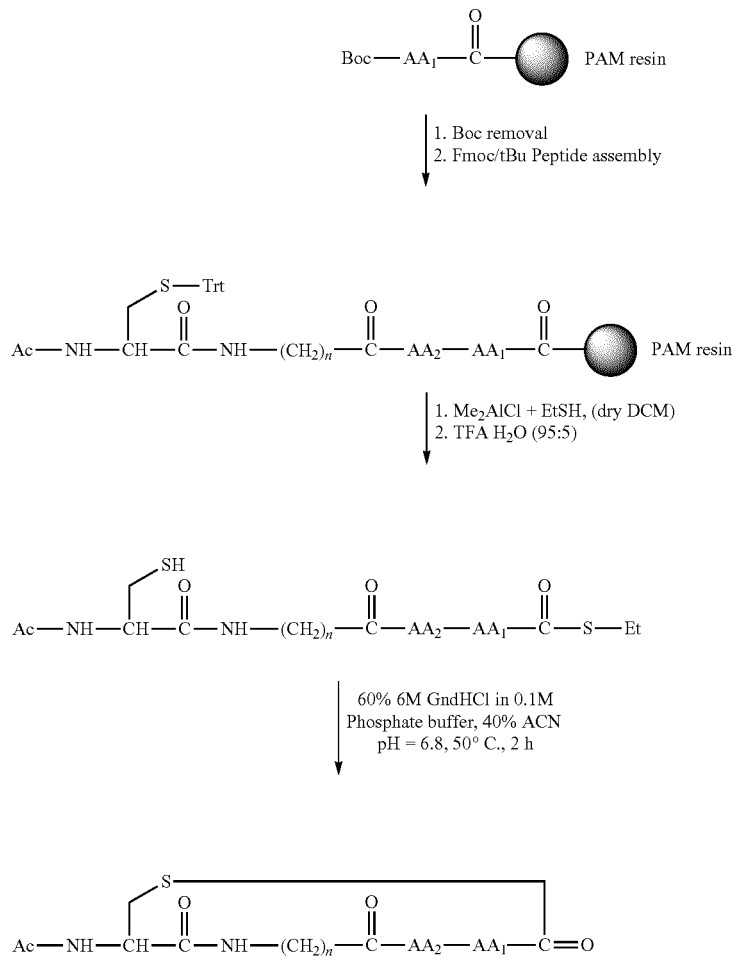

$AA_1$, $AA_2$ = Leu, Phe, Ile n = 1-7

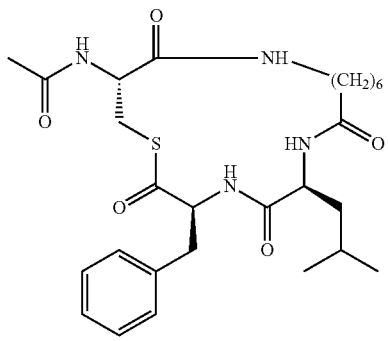

AgrC-II IC$_{50}$ = 1933 nM

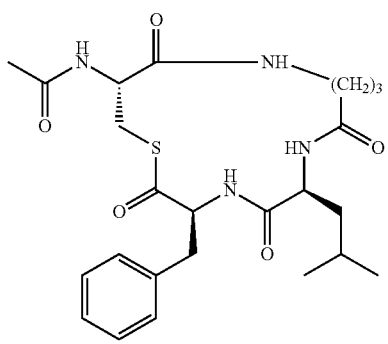

AgrC-II IC$_{50}$ = 2203 nM
AgrC-III IC$_{50}$ = 3617 nM
AgrC-IV IC$_{50}$ = 352 nM

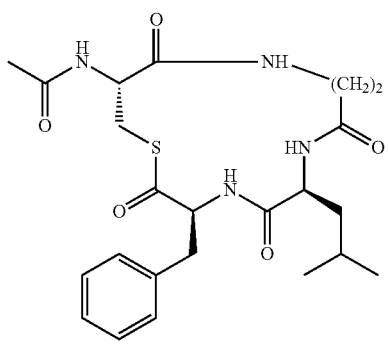

AgrC-III IC$_{50}$ = 708 nM

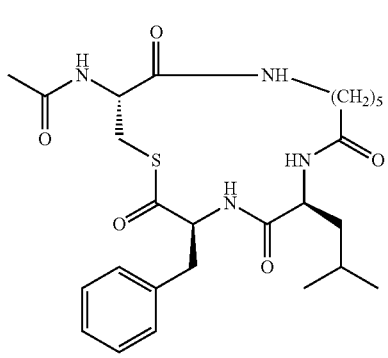

AgrC-II IC$_{50}$ = 3478 nM
AgrC-III IC$_{50}$ = 1063 nM

-continued

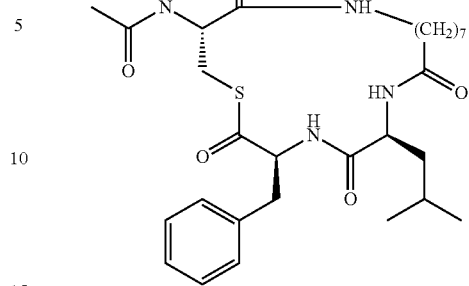

AgrC-III IC$_{50}$ = 1073 nM

TABLE 9

Comparison of Relative Inhibition of Compounds of Formula V for AgrC groups

| Compound designation | AgrC-I[a] % Activation | AgrC-II[a] % Activation | AgrC-III[a] % Activation | AgrC-IV[a] % Activation |
|---|---|---|---|---|
| n1LF | 114 ± 21 | 117 ± 25 | 137 ± 14 | 115 ± 9 |
| n2LF | 104 ± 15 | 2 ± 0 | 138 ± 9 | 99 ± 14 |
| n3LF | 17 ± 7 | 28 ± 10 | 13 ± 7 | 6 ± 3 |
| n4LF | 99 ± 30 | 88 ± 52 | 120 ± 28 | 110 ± 14 |
| n5LF | 76 ± 42 | 78 ± 37 | 6 ± 3 | 120 ± 19 |
| n6LF | 69 ± 20 | 3 ± 0 | 6 ± 3 | 80 ± 21 |
| n7LF | 54 ± 34 | 43 ± 25 | 7 ± 3 | 98 ± 14 |
| n1LL | 108 ± 14 | 72 ± 20 | 139 ± 35 | 119 ± 17 |
| n2LL | 87 ± 20 | 83 ± 30 | 88 ± 9 | 110 ± 7 |
| n3LL | 86 ± 24 | 62 ± 14 | 113 ± 10 | 119 ± 11 |
| n4LL | 80 ± 9 | 75 ± 22 | 83 ± 16 | 102 ± 10 |
| n5LL | 87 ± 10 | 88 ± 24 | 105 ± 40 | 119 ± 17 |
| n6LL | 81 ± 18 | 82 ± 40 | 107 ± 23 | 129 ± 15 |
| n7LL | 103 ± 64 | 76 ± 28 | 117 ± 28 | 122 ± 15 |
| n1LI | 90 ± 13 | 82 ± 22 | 141 ± 32 | 141 ± 18 |
| n2LI | 89 ± 61 | 44 ± 23 | 135 ± 42 | 130 ± 17 |
| n3LI | 72 ± 19 | 64 ± 18 | 106 ± 13 | 126 ± 18 |
| n4LI | 55 ± 8 | 36 ± 18 | 106 ± 48 | 132 ± 18 |
| n5LI | 60 ± 6 | 31 ± 12 | 43 ± 9 | 70 ± 28 |
| n6LI | 68 ± 16 | 41 ± 13 | 93 ± 26 | 133 ± 17 |
| n7LI | 126 ± 57 | 92 ± 72 | 109 ± 19 | 103 ± 4 |

[a]% Activation is a comparison of fluorescence of treated bacteria to non-treated wild-type bacteria (*S. Aureus*) which produce native-ligand which activates QS in the absence of an inhibitor; a lower % activation indicates more potent inhibition.

REFERENCES (1) Ng, W. L.; Bassler, B. L. *Annu. Rev. Genet.* 2009, 43, 197-222.

(2) Bassler, B. L.; Losick, R. *Cell* 2006, 125, 237-246.

(3) Camilli, A.; Bassler, B. L. *Science* 2006, 311, 1113-1116.

(4) Eberhard, A.; Burlingame, A. L.; Eberhard, C.; Kenyon, G. L.; Nealson, K. H.; Oppenheimer, N. J. *Biochemistry* 1981, 20, 2444-2449.

(5) Marketon, M. M.; Gronquist, M. R.; Eberhard, A.; Gonzalez, J. E. *J. Bacteriol.* 2002, 184, 5686-5695.

(6) Joint, I.; Downie, J. A.; Williams, P. *Philos. Trans. R. Soc. Lond. B. Biol. Sci.* 2007, 362, 1115-1117.

(7) von Bodman, S. B.; Willey, J. M.; Diggle, S. P. *J. Bacteriol.* 2008, 190, 4377-4391.

(8) Boyer, M.; Wisniewski-Dye, F. *FEMS Microbiol Eco/* 2009, 70, 1-19.

(9) De Kievit, T. R.; Iglewski, B. H. *Infect. Immun.* 2000, 68, 4839-4849.

(10) Bjarnsholt, T.; Givskov, M. *Anal. Bioanal. Chem.* 2007, 387, 409-414.

(11) Hibbing, M. E.; Fuqua, C.; Parsek, M. R.; Peterson, S. B. *Nat. Rev. Microbiol.* 2010, 8, 15-25.
(12) Njoroge, J.; Sperandio, V. *EMBO Mol. Med.* 2009, 1, 201-210.
(13) Wright, G. D. *Curr. Opin. Chem. Biol.* 2003, 7, 563-569.
(14) Walsh, C. *Nature* 2000, 406, 775-781.
(15) Rotun, S. S.; McMath, V.; Schoonmaker, D. J.; Maupin, P. S.; Tenover, F. C.; Hill, B. C.; Ackman, D. M. *Emerg. Infect. Dis.* 1999, 5, 147-149.
(16) Chambers, H. F.; Deleo, F. R. *Nat. Rev. Microbiol.* 2009, 7, 629-641.
(17) Deleo, F. R.; Chambers, H. F. *J. Clin. Invest.* 2009, 119, 2464-2474.
(18) Recsei, P.; Kreiswirth, B.; O'Reilly, M.; Schlievert, P.; Gruss, A.; Novick, R. P. *Mol. Gen. Genet.* 1986, 202, 58-61.
(19) Pragman, A. A.; Schlievert, P. M. *FEMS Immunol. Med. Microbiol.* 2004, 42, 147-154.
(20) George, E. A.; Muir, T. W. *ChemBioChem* 2007, 8, 847-855.
(21) Lina, G.; Jarraud, S.; Ji, G. Y.; Greenland, T.; Pedraza, A.; Etienne, J.; Novick, R. P.; Vandenesch, F. *Mol. Microbiol.* 1998, 28, 655-662.
(22) Novick, R. P.; Ross, H. F.; Projan, S. J.; Kornblum, J.; Kreiswirth, B.; Moghazeh, S. *EMBO J.* 1993, 12, 3967-3975.
(23) Ji, G.; Beavis, R.; Novick, R. P. *Science* 1997, 276, 2027-2030.
(24) McDowell, P.; Affas, Z.; Reynolds, C.; Holden, M. T.; Wood, S. J.; Saint, S.; Cockayne, A.; Hill, P. J.; Dodd, C. E.; Bycroft, B. W.; Chan, W. C.; Williams, P. *Mol. Microbiol.* 2001, 41, 503-512.
(25) Jarraud, S.; Lyon, G. J.; Figueiredo, A. M.; Gerard, L.; Vandenesch, F.; Etienne, J.; Muir, T. W.; Novick, R. P. *J. Bacteriol.* 2000, 182, 6517-6522.
(26) Jarraud, S.; Mougel, C.; Thioulouse, J.; Lina, G.; Meugnier, H.; Forey, F.; Nesme, X.; Etienne, J.; Vandenesch, F. *Infect. Immun.* 2002, 70, 631-641.
(27) Holtfreter, S.; Grumann, D.; Schmudde, M.; Nguyen, H. T. T.; Eichler, P.; Strommenger, B.; Kopron, K.; Kolata, J.; Giedrys-Kalemba, S.; Steinmetz, I.; Witte, W.; Broker, B. M. *J. Clin. Microbiol.* 2007, 45, 2669-2680.
(28) Limbago, B.; Fosheim, G. E.; Schoonover, V.; Crane, C. E.; Nadle, J.; Petit, S.; Heltzel, D.; Ray, S. M.; Harrison, L. H.; Lynfield, R.; Dumyati, G.; Townes, J. M.; Schaffner, W.; Mu, Y.; Fridkin, S. K. *J. Clin. Microbiol.* 2009, 47, 1344-1351.
(29) Li, J. R.; Wang, W. L.; Xu, S. X.; Magarvey, N. A.; McCormick, J. K. *Proc. Natl. Acad. Sci. U.S.A.* 2011, 108, 3360-3365.
(30) Musser, J. M.; Schlievert, P. M.; Chow, A. W.; Ewan, P.; Kreiswirth, B. N.; Rosdahl, V. T.; Naidu, A. S.; Witte, W.; Selander, R. K. *Proc. Natl. Acad. Sci. U.S.A.* 1990, 87, 225-229.
(31) Galloway, W. R.; Hodgkinson, J. T.; Bowden, S. D.; Welch, M.; Spring, D. R. *Chem. Rev.* 2011, 111, 28-67.
(32) Geske, G. D.; O'Neill, J. C.; Blackwell, H. E. *Chem. Soc. Rev.* 2008, 37, 1432-1447.
(33) Persson, T.; Givskov, M.; Nielsen, J. *Curr. Med. Chem.* 2005, 12, 3103-3115.
(34) Stevens, A. M.; Queneau, Y.; Soulere, L.; von Bodman, S.; Doutheau, A. *Chem. Rev.* 2011, 111, 4-27.
(35) Amara, N.; Krom, B. P.; Kaufmann, G. F.; Meijler, M. M. *Chem. Rev.* 2011, 111, 195-208.
(36) Sintim, H. O.; Smith, J. A.; Wang, J.; Nakayama, S.; Yan, L. *Future Med. Chem.* 2010, 2, 1005-1035.
(37) Rasko, D. A.; Sperandio, V. *Nat. Rev. Drug Disc.* 2010, 9, 117-128.
(38) Kaufmann, G. F.; Park, J.; Janda, K. D. *Exp. Opin. Biol. Ther.* 2008, 8, 719-724.
(39) Geske, G. D.; O'Neill, J. C.; Miller, D. M.; Mattmann, M. E.; Blackwell, H. E. *J. Am. Chem. Soc.* 2007, 129, 13613-13625.
(40) Geske, G. D.; O'Neill, J. C.; Miller, D. M.; Wezeman, R. J.; Mattmann, M. E.; Lin, Q.; Blackwell, H. E. *ChemBioChem* 2008, 9, 389-400.
(41) Mattmann, M. E.; Blackwell, H. E. *J. Org. Chem.* 2010, 75, 6737-6746.
(42) Palmer, A. G.; Streng, E.; Blackwell, H. E. *ACS Chem. Biol.* 2011, 6, 1348-1356.
(43) Stacy, D. M.; Welsh, M. A.; Rather, P. N.; Blackwell, H. E. *ACS Chem. Biol.* 2012, in press.
(44) Park, J.; Jagasia, R.; Kaufmann, G. F.; Mathison, J. C.; Ruiz, D. I.; Moss, J. A.; Meijler, M. M.; Ulevitch, R. J.; Janda, K. D. *Chem. Biol.* 2007, 14, 1119-1127.
(45) Mayville, P.; Ji, G.; Beavis, R.; Yang, H.; Goger, M.; Novick, R. P.; Muir, T. W. *Proc. Natl. Acad. Sci. U.S.A.* 1999, 96, 1218-1223.
(46) Lyon, G. J.; Mayville, P.; Muir, T. W.; Novick, R. P. *Proc. Natl. Acad. Sci. U.S.A.* 2000, 97, 13330-13335.
(47) Wright, J. S.; Jin, R.; Novick, R. P. *Proc. Natl. Acad. Sci. U.S.A.* 2005, 102, 1691-1696.
(48) Fleming, V.; Feil, E.; Sewell, A. K.; Day, N.; Buckling, A.; Massey, R. C. *J. Bacteriol.* 2006, 188, 7686-7688.
(49) Lyon, G. J.; Wright, J. S.; Muir, T. W.; Novick, R. P. *Biochemistry* 2002, 41, 10095-10104.
(50) Scott, R. J.; Lian, L. Y.; Muharram, S. H.; Cockayne, A.; Wood, S. J.; Bycroft, B. W.; Williams, P.; Chan, W. C. *Bioorg. Med. Chem. Lett.* 2003, 13, 2449-2453.
(51) George, E. A.; Novick, R. P.; Muir, T. W. *J. Am. Chem. Soc.* 2008, 130, 4914-4924.
(52) Fowler, S. A.; Stacy, D. M.; Blackwell, H. E. *Org. Lett.* 2008, 10, 2329-2332.
(53) Chan, W. C.; Coyle, B. J.; Williams, P. *J. Med. Chem.* 2004, 47, 4633-4641.
(54) Lyon, G. J.; Novick, R. P. *Peptides* 2004, 25, 1389-1403.
(55) Thoendel, M.; Kavanaugh, J. S.; Flack, C. E.; Horswill, A. R. *Chem. Rev.* 2011, 111, 117-151.
(56) Gorske, B. C.; Blackwell, H. E. *Org. Biomol. Chem.* 2006, 4, 1441-1445.
(57) Campbell, J.; Lin, Q.; Geske, G. D.; Blackwell, H. E. *ACS Chem. Biol.* 2009, 4, 1051-1059.
(58) Kirchdoerfer, R. N.; Garner, A. L.; Flack, C. E.; Mee, J. M.; Horswill, A. R.; Janda, K. D.; Kaufmann, G. F.; Wilson, I. A. *J. Biol. Chem.* 2011, 286, 17351-17358.
(59) Malone, C. L.; Boles, B. R.; Horswill, A. R. *Appl. Environ. Microbiol.* 2007, 73, 6036-6044.
(60) Schlievert, P. M.; Blomster, D. A. *J. Infect. Dis.* 1983, 147, 236-242.
(61) Otto, M.; Echner, H.; Voelter, W.; Gotz, F. *Infect. Immun.* 2001, 69, 1957-1960.
(62) Sewing, A.; Hilvert, D. *Angew. Chem. Int. Ed.* 2001, 40, 3395-3396.
(63) Swinnen, D.; Hilvert, D. *Org. Lett.* 2000, 2, 2439-2442.
(64) Dawson, P. E.; Muir, T. W.; Clarklewis, I.; Kent, S. B. H. *Science* 1994, 266, 776-779.
(65) Blevins, J. S.; Beenken, K. E.; Elasri, M. O.; Hurlburt, B. K.; Smeltzer, M. S. *Infect. Immun.* 2002, 70, 470-480.
(66) Lopes, M. D.; Teixeira, L. M. *Rev. Microbiol.* 1992, 23, 59-65.
(67) Naider, F., and Goodman, M. (2002) Historical Aspects, in Synthesis of Peptides and Peptidomimetics (Goodman, M., Toniolo, C., Moroder, L., and Felix, A., Eds.) 4th ed., pp 1-16, Thieme, Stuttgart N.Y.

(68) Adessi, C., and Soto, C. (2002) Converting a peptide into a drug: Strategies to improve stability and bioavailability, Curr Med Chem 9, 963-978.

(69) Rezai, T., Bock, J. E., Zhou, M. V., Kalyanaraman, C., Lokey, R. S., and Jacobson, M. P. (2006) Conformational flexibility, internal hydrogen bonding, and passive membrane permeability: Successful in silico prediction of the relative permeabilities of cyclic peptides, J Am Chem Soc 128, 14073-14080.

(70) White, T. R., Renzelman, C. M., Rand, A. C., Rezai, T., McEwen, C. M., Gelev, V. M., Turner, R. A., Linington, R. G., Leung, S. S. F., Kalgutkar, A. S., Bauman, J. N., Zhang, Y. Z., Liras, S., Price, D. A., Mathiowetz, A. M., Jacobson, M. P., and Lokey, R. S. (2011) On-resin N-methylation of cyclic peptides for discovery of orally bioavailable scaffolds, Nat Chem Biol 7, 810-817.

(71) Boeglin, D., Xiang, Z., Sorenson, N. B., Wood, M. S., Haskell-Luevano, C., and Lubell, W. D. (2006) Aza-scanning of the potent melanocortin receptor agonist Ac-His-D-Phe-Arg-Trp-$NH_2$, Chem Bio Drug Des 67, 275-283.

(72) Walensky, L. D., Kung, A. L., Escher, I., Malia, T. J., Barbuto, S., Wright, R. D., Wagner, G., Verdine, G. L., and Korsmeyer, S. J. (2004) Activation of Apoptosis in Vivo by a Hydrocarbon-Stapled BH3 Helix, Science 305, 1466-1470.

(73) Beck, J. G., Chatterjee, J., Laufer, B., Kiran, M. U., Frank, A. O., Neubauer, S., Ovadia, O., Greenberg, S., Gilon, C., Hoffman, A., and Kessler, H. (2012) Intestinal Permeability of Cyclic Peptides: Common Key Backbone Motifs Identified, J Am Chem Soc 134, 12125-12133.

(74) Ovadia, O.; Greenberg, S.; Laufer, B.; Gilon, C.; Hoffman, A.; Kessler, H., Improvement of drug-like properties of peptides: the somatostatin paradigm. Expert Opin Drug Dis 2010, 5, (7), 655-671.

(75) Zuckermann, R. N.; Kerr, J. M.; Kent, S. B. H.; Moos, W. H., Efficient Method for the Preparation of Peptoids [Oligo (N-Substituted Glycines)] by Submonomer Solid-Phase Synthesis. J Am Chem Soc 1992, 114, (26), 10646-10647.

(76) Pedroso, E.; Grandas, A.; Delasheras, X.; Eritja, R.; Giralt, E., Diketopiperazine Formation in Solid-Phase Peptide-Synthesis Using P-Alkoxybenzyl Ester Resins and Fmoc-Amino Acids. Tetrahedron Lett 1986, 27, (6), 743-746.

(77) Khosla, M. C.; Smeby, R. R.; Bumpus, F. M., Failure sequence in solid-phase peptide synthesis due to the presence of an N-alkylamino acid. J Am Chem Soc 1972, 94, (13), 4721-4724.

(78) Schnolzer, M., Alewood, P., Jones, A., Alewood, D., and Kent, S. B. H. 2007, In situ neutralization in boc-chemistry solid phase peptide synthesis—Rapid, high yield assembly of difficult sequences, Int J Pept Res Ther 13, 31-44.

(79) Cardenal, C., Vollrath, S. B. L., Schepers, U., and Brase, S. 2012, Synthesis of Functionalized Glutamine- and Asparagine-Type Peptoids—Scope and Limitations, Helvetica Chimica Acta 95, 2237-2248.

(80) Culf A. S. and Ouellette, R. J. (2010) Solid-Phase synthesis of N-substituted Glycine Oligomers (alpha-peptoids) and derivatives.

The invention claimed is:

1. A compound of formula:

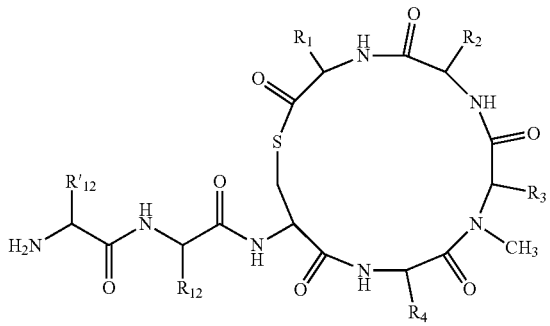

or salts thereof where:
$R_1$ and $R_2$ are iso-butyl groups;
$R_3$ is a benzyl group;
$R_4$ is selected from a C1-C3 alkyl group or a —$CH_2$—COOH group, and
$R_{12}$ and $R'_{12}$ are independently selected from a C1-C4 alkyl group, a —$CH_2$—CO—$NH_2$ group or a —$CH_2$—$CH_2$—CO—$NH_2$ group; and
wherein each amino acid is an L-amino acid.

2. The compound or salt of claim 1, wherein $R_4$ is a —$CH_2$—COOH group.

3. The compound or salt of claim 1, wherein $R_4$ is a methyl group.

4. The compound or salt of claim 1, wherein $R'_{12}$ is a C1-C4 alkyl group.

5. The compound or salt of claim 1, wherein $R'_{12}$ is a methyl group.

6. The compound or salt of claim 1, wherein $R_{12}$ is a sec-butyl group.

7. The compound or salt of claim 1, wherein $R'_{12}$ is a —$CH_2$—$CH_2$—CO—$NH_2$ group.

8. The compound or salt of claim 1, wherein $R_{12}$ is a C1-C4 alkyl group.

9. The compound or salt of claim 1, wherein $R_{12}$ is a methyl group.

10. The compound or salt of claim 1, wherein $R_{12}$ is a sec-butyl group.

11. The compound or salt of claim 1, wherein $R_{12}$ is a —$CH_2$—$CH_2$—CO—$NH_2$ group.

12. The compound or salt of claim 1, wherein $R'_{12}$ is sec-butyl, and $R_{12}$ is a —$CH_2$—$CH_2$—CO—$NH_2$ group.

13. The compound or salt of claim 1, wherein $R'_{12}$ is methyl, and $R_{12}$ is a —$CH_2$—$CH_2$—CO—$NH_2$ group.

14. The compound or salt of claim 1, wherein $R'_{12}$ is sec-butyl group, and $R_{12}$ is a methyl group.

15. The compound or salt of claim 1, wherein $R'_{12}$ and $R_{12}$ are both methyl groups.

16. The compound or salt of claim 1, wherein $R'_{12}$ is sec-butyl, $R_{12}$ is a —$CH_2$—$CH_2$—CO—$NH_2$ group, and $R_4$ is a —$CH_2$—COOH group.

17. The compound or salt of claim 1, wherein $R'_{12}$ is a sec-butyl group, $R_{12}$ is a —$CH_2$—$CH_2$—CO—$NH_2$ group, and $R_4$ is a methyl group.

18. The compound or salt of claim 1, wherein $R'_{12}$ is a methyl group, $R_{12}$ is a —$CH_2$—$CH_2$—CO—$NH_2$ group, and $R_4$ is a methyl group.

19. The compound or salt of claim 1, wherein $R'_{12}$ is a sec-butyl group, $R_{12}$ is a methyl group, and $R_4$ is a methyl group.

20. The compound or salt of claim 1, wherein $R'_{12}$ is a methyl group, $R_{12}$ is a methyl group, and $R_4$ is a methyl group.

21. A pharmaceutical composition which comprises a therapeutically effective amount of one or more compounds or salts of claim 1 and a pharmaceutically acceptable carrier.

22. A method for attenuating virulence in *Staphylococcus* which comprises the step of contacting the bacterium with one or more compounds or salts selected from the compounds or salts of claim 1.

23. The method of claim 22, wherein the production of toxic shock syndrome toxin-1 is attenuated.

24. A method of treating staphylococcal infection which comprises administering to an individual in need of treatment a therapeutically effective amount of one or more compounds or salts of claim 1.

25. The method of claim 24, wherein the staphylococcal infection is a *Staphylococcus aureus* infection.

26. The method of claim 25, wherein the infection is toxic shock syndrome.

* * * * *